United States Patent
Millenbaugh

(10) Patent No.: US 11,298,561 B2
(45) Date of Patent: Apr. 12, 2022

(54) METHOD OF TREATING MULTI-DRUG RESISTANCE BIOFILM USING TARGETED LASER AND ANTIBIOTICS

(71) Applicant: The United States of America Represented by the Secretary of Navy, Silver Spring, MD (US)

(72) Inventor: Nancy Millenbaugh, San Antonio, TX (US)

(73) Assignee: The United States of America As Represented by the Secretary of the Navy, Arlinton, VA (US)

( * ) Notice: Subject to any disclaimer, the term of this patent is extended or adjusted under 35 U.S.C. 154(b) by 0 days.

(21) Appl. No.: 16/403,564

(22) Filed: May 5, 2019

(65) Prior Publication Data

US 2019/0255349 A1    Aug. 22, 2019

Related U.S. Application Data

(60) Continuation-in-part of application No. 15/974,294, filed on May 18, 2018, now Pat. No. 10,835,755, which is a division of application No. 13/900,994, filed on May 23, 2013, now Pat. No. 9,993,660.

(60) Provisional application No. 62/667,570, filed on May 26, 2018.

(51) Int. Cl.
| | | |
|---|---|---|
| *A61K 9/14* | (2006.01) | |
| *A61K 45/06* | (2006.01) | |
| *A61K 9/51* | (2006.01) | |
| *A61N 5/06* | (2006.01) | |
| *A61K 47/69* | (2017.01) | |
| *A61K 47/68* | (2017.01) | |
| *A61K 41/00* | (2020.01) | |
| *A61N 5/067* | (2006.01) | |

(52) U.S. Cl.
CPC .......... *A61N 5/062* (2013.01); *A61K 41/0052* (2013.01); *A61K 45/06* (2013.01); *A61K 47/6835* (2017.08); *A61K 47/6923* (2017.08); *A61N 5/0624* (2013.01); *A61N 2005/067* (2013.01)

(58) Field of Classification Search
CPC .................. A61K 9/14; A61K 41/2257; A61K 47/48561; A61K 45/06; A61K 9/16; A61K 9/51
USPC .......... 424/130.1, 163.1, 164.1, 178.1, 184.1, 424/234.1
See application file for complete search history.

*Primary Examiner* — Rodney P Swartz
(74) *Attorney, Agent, or Firm* — Albert M. Churilla; Ning Yang; Diane Tso

(57) ABSTRACT

This application describes a method of using gold nanoparticle (GNP)-targeted pulsed laser technology to enhance antibiotic efficacy against multidrug resistant biofilms. The application also teaches a method for treating topic wound infection using GNP-targeted laser therapy combined with antibiotics treatments.

23 Claims, 26 Drawing Sheets

FIG. 17

Figure 1:
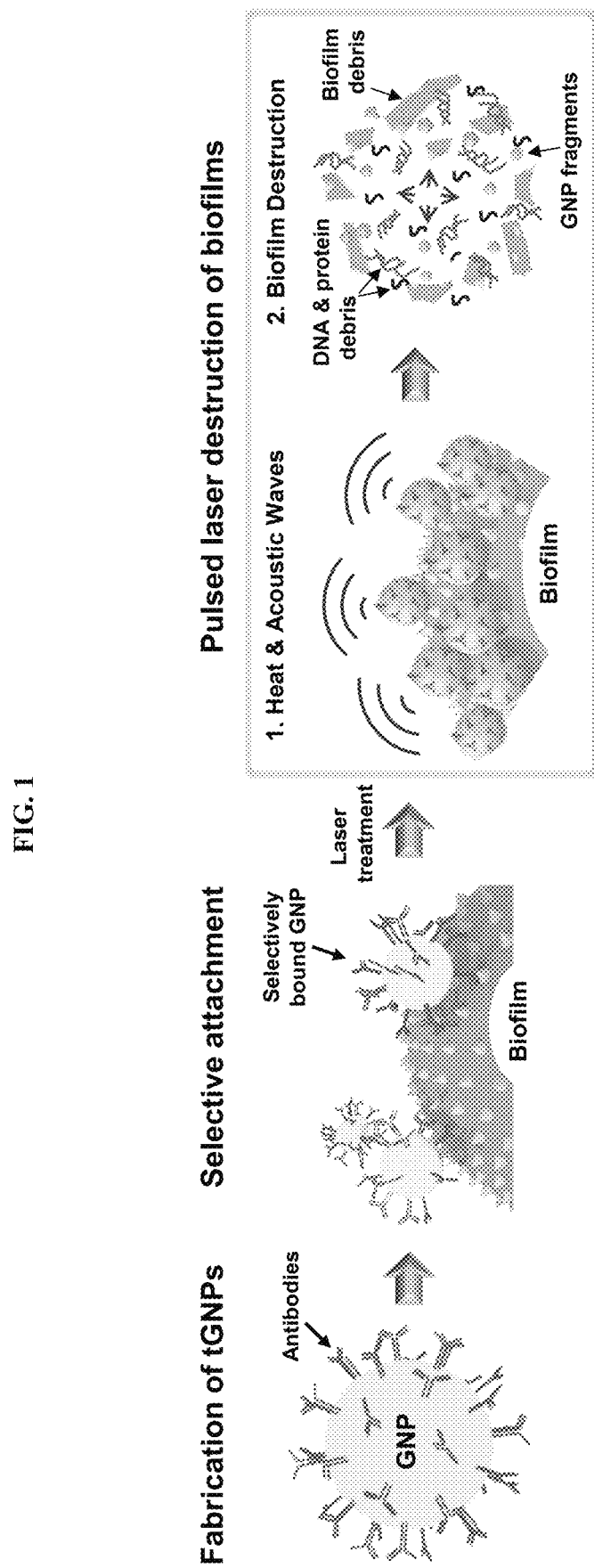

Table 2. Topical Antibiotic Products Available for Treating Chronic Wounds

| Product | Formulations(s) | Bacterial spectrum | Advantages | Disadvantages | Cost[a] | Indications[b] and comments |
|---|---|---|---|---|---|---|
| Bacitracin[c] | Ointment, 500 units/g; and powder combinations with neomycin, polymixin B, and zinc | Many gram-positive organisms, including aerobic staphylococci and streptococci, corynebacteria, anaerobic cocci, and clostridia; inactive against most gram-negative organisms | Activity not impaired by blood, pus, necrotic tissue, or large bacterial inocula; resistance is rare but increasing among staphylococci; no cross-resistance with other antibiotics; minimal absorption | May cause allergic reactions, contact dermatitis, and (rarely) anaphylactic reactions; may lead to overgrowth of drug-resistant organisms, including fungi | $ | Widely used for many years; indicated for prevention of infection in minor skin injuries |
| Fusidic acid | Cream, 2%; ointment, 2%; and gel, 2% | *Staphylococcus aureus*, streptococci (in topical concentrations), corynebacteria and clostridia | Penetrates intact and damaged skin as well as crust and cellular debris | Occasional hypersensitivity reactions; resistance among staphylococci is emerging; must apply 3 times daily | $$ | Not available in the United States |

FIG 17 (continued)

| | | | | | |
|---|---|---|---|---|---|
| Gentamicin | Cream, 0.1%; and ointment, 0.1% | Streptococci, staphylococci, *Pseudomonas aeruginosa, Enterbacter aerogenes, Escherichia coli, Proteus vulgaris,* and *Klebsiella pneumoniae* | Broad spectrum; inexpensive | Must be applied 3–4 times daily; may drive resistance to an agent used systemically | $ | Indicated for primary skin infections (pyodermas) and for secondary skin infections, including infected excoriations, and for bacterial superinfections |
| Mafenide acetate | Solution, 5%; and cream, 85 mg/g | A sulfonamide that is bacteriostatic against many organisms, including *P. aeruginosa*, and some gram-positive organisms, but minimal activity against staphylococci and some obligate anaerobes | Remains active in the presence of pus and serum, and its activity is not affected by acidity of environment | Systemic absorption may occur; drug and metabolites may inhibit carbonic anhydrase, potentially causing metabolic acidosis; use cautiously in patients with renal impairment; pain on application; hypersensitivity reactions | $$$ | Indicated as adjunctive therapy in second- and third-degree burns; may be used in rapidly progressing bacterial necrotizing fasciitis; limited use in other wounds |
| Metronidazole | Cream, 0.75%; gel, 1%; lotion, 0.75% | Many clinically important | May reduce odor associated with anaerobic | Relatively expensive; systemic | $-$$ | Indicated for inflammatory |

FIG 17 (continued)

| | | anaerobic bacteria | infections; application only 1–2 times daily | formulations available; could drive resistance to these | | papules and pustules of rosacea |
|---|---|---|---|---|---|---|
| Mupirocin and mupirocin calcium | Ointment, 2%; for mupirocin calcium, cream, 2.15%;[c] and nasal ointment, 2.15%;[c] (equivalent to 2% mupirocin) | Gram-positive aerobes, including S. aureus (most MRSA), Staphylococcus epidermidis, Staphylococcus saprophyticus, and streptococci (groups A, B, C, and G) but not enterococci, some gram-negative aerobes (not P. aeruginosa), corynebacteria, and obligate anaerobes | Minimal potential for allergic reactions | Rare local burning and irritation; applying ointment to large wounds in azotemic patients can cause accumulation of polyethylene glycol; long-term use can lead to resistance among staphylococci, which is increasing | $$ | Indicated for topical treatment of impetigo and eradication of nasal colonization with S. aureus |
| Neomycin sulfate[e] | Powder; cream, 0.5%, combinations with polymixin B and pramoxine; and ointment, 0.5%, | Good for gram-negative organisms but not P. aeruginosa; active against some gram-positive bacteria, | Low cost; applied only 1–3 times daily; may enhance reepithelialization | Topical powder in wound irrigating solution may cause systemic toxicity (FDA banned); use other formulations | $ | Use of topical powder alone or in solution is not recommended; cream and ointment, in combination with other agents are indicated for prevention of |

FIG 17 (continued)

| | | | | |
|---|---|---|---|---|
| | combinations with bacitracin, polymixin B, lidocaine, and pramoxine | including *S. aureus*, but streptococci are generally resistant; inactive against obligate anaerobes | | cautiously on large wounds, especially with azotemia; hypersensitivity reaction in 1%–6%, often with chronic use or history of allergies | infection in minor skin injuries |
| Nitrofurazone | Solution, 0.2%; ointment, 0.2%; and cream, 0.2% | Broad gram-positive and gram-negative activity, including *S. aureus* and streptococci, but not *P. aeruginosa* | Used mainly for burn wounds | Hypersensitivity reactions; polyethylene glycols (in some formulations) may be absorbed and can cause problems in azotemic patients | $$ Indicated as adjunctive to prevent infections in patients with second- and third-degree burns |
| Polymixin B | Cream, 5000 units/g or 10,000 units/g, in combination with other agents | Bactericidal against many gram-negative organisms, including *P. aeruginosa*; minimal activity against gram-positive bacteria; activity may be | Inexpensive | Some hypersensitivity and neurological or renal adverse reactions reported; may show cross-reaction with bacitracin | $ Only available in combination with other agents, including bacitracin and neomycin; indicated for prevention of infection in minor skin injuries |

FIG 17 (continued)

| | | | | |
|---|---|---|---|---|
| Retapamulin | Ointment, 1% | Active against staphylococci (but uncertain for MRSA) and streptococci and some obligate anaerobes | Not evaluated for use on mucosal surfaces; may cause local irritation | $$$ | Indicated for impetigo, due to *S. aureus* (methicillin-susceptible only) or *S. pyogenes* |
| Silver sulfadiazine | Cream, 1% | A sulfonamide; the released silver ions are the primary active ingredient; active against many gram-positive and gram-negative organisms, including *P. aeruginosa* | Applied only once or twice daily; soothing application; low rate of hypersensitivity reaction | $ | Indicated as adjunctive treatment to prevent infections in patients with second- and third-degree burns |
| Sulfacetamide Na+ | Lotion, 10% | Bacteriostatic against many gram-positive and gram-negative pathogens; neutralized by divalent cations | Broad spectrum; can be combined with sulphur | Systemic absorption and rarely severe side effects occur with application to large, denuded areas; hypersensitivity reactions may occur | $$$ | Indicated for secondary bacterial skin infections due to susceptible organisms and for acne vulgaris in adults |

FIG 17 (continued)

NOTE. There are no published studies supporting the use of topical erythromycin, clindamycin, aminoglycosides other than neomycin, gramicidin or tetracyclines for treating chronically infected wounds. FDA, US Food and Drug Administration; MRSA, methicillin-resistant *S. aureus*.
[a] Costs are approximate in US$ per day for treating 100-cm$^2$ wound, as follows: $, <$3; $$, $3-$15; and $$$, >$15.
[b] FDA-approved indications.
[c] Available without prescription.

FIG 18 (continued)

| | | | | | |
|---|---|---|---|---|---|
| Chlorhexidine gluconate | Solution, 2% and 4%; liquid, 2% and 4%; hand rinse, 0.5%, wipes, 0.5%; sponge/brush, 4%; and foam, 4% | Active against gram-positive bacteria (eg, *Staphylococcus aureus*) and gram-negative bacteria, including *P. aeruginosa* | Persistent activity up to 6 h after application; few adverse effects | Hypersensitivity, including anaphylaxis, generalized urticaria, bronchospasm, cough, dyspnea, wheezing and malaise; may cause serious injury to the eye and middle ear; avoid contact with face or head; some resistance reported | $ | 2% Chlorhexidine indicated as surgical hand scrub, hand wash, preoperative skin, skin wound cleanser, and skin cleaner; polyhexanide is a similar newer biguanide |
| Hexachlorophene | Liquid, 3%; foam, 0.23% with 56% alcohol | Biguanide that is bacteriostatic against *Staphylococcus* species and other gram-positive bacteria | May retain residual effect on skin for several days | Rapidly absorbed and may result in toxic blood levels; application to burns has resulted in neurotoxicity and death; may cause central nervous system stimulation and convulsions, dermatitis, and photosensitivity reactions | $$$ | Not recommended for routine use on wounds because of potential toxicity |

FIG 18 (continued)

| | | | | | |
|---|---|---|---|---|---|
| Iodine compounds and iodine tincture[c] | Solution, 2% and 2.4%; and NaI strong iodine (Lugols), 5% and 10% KI; for iodine tincture, 2% and 2.4% NaI with 47% alcohol; and 7%, 5% KI in 83% EtOH | Microbicidal against bacteria, fungi, viruses, spores, protozoa, and yeasts | Broad spectrum | Highly toxic if ingested or significantly absorbed; do not use with occlusive dressings; causes pain and stains skin and clothing; use cautiously in patients with thyroid disorders | $ Iodine compounds are now rarely used for wound management; cadexomer iodine and povidone iodine products are less toxic |
| Povidone iodine[c] | Ointment, 1%, 4.7% and 10%; solution, 1% and 10%; and wash, scrub, cleanser, gel, aerosol, gauze pad, swab, and others | Broad spectrum includes *S. aureus* and enterococci; active ingredient is liberated free iodine; shares spectrum but is less potent than iodine | Less irritating to skin and allergenic than iodine. Can be covered with dressings. Clinically significant resistance very rare | Antibacterial action requires at least 2 min contact; may cause stinging and erythema; effect may not persist, and efficacy may be reduced in body fluids; prolonged use may cause metabolic acidosis; stains skin and clothing; possible interaction with starches in dressings | $ Indicated for perioperative skin cleansing and for cleansing and prevention of infection in superficial burns, incisions, and other superficial wounds |
| Sodium hypochlorite[c] (Dakin's solution and EUSOL) | Solution, 0.0125%, 0.125%, 0.25%, and 0.5% | Vegetative bacteria, viruses and some spores and fungi | Inexpensive. No known systemic toxicity | May require prolonged contact for antibacterial action; inactivated by pus; toxic to fibroblasts and keratinocytes, and may | $ Concentrations ≤0.025% may be useful to reduce bioburden |

FIG 18 (continued)

| | | | | | |
|---|---|---|---|---|---|
| Hydrogen peroxide[c] | Solution, 1% and 3%; and cream, 1% | Oxidizing agent active against many gram-positive and gram-negative bacteria | Broad-spectrum, bactericidal, inexpensive; no known resistance | May cause some discomfort | $ | Commonly used, but few clinical studies |
| Silver nitrate | Solution 0.5%, 10%, 25%, and 50%; ointment, 10%; and swabs, 25%–50% | Silver ions are bactericidal against a broad spectrum of gram-positive and gram-negative bacteria | Low cost; easily applied | Painful on application; stains tissues; may delay healing; concentrations >0.5% cause cauterization; inactivated by wound exudates and chlorine | $ | Although it was previously widely used, it has now been largely replaced by other compounds, including newer silver dressings |
| Silver dressings | At least 6 approved products with different properties | Slowly released silver ions have broad-spectrum, including MRSA and VRE | Provide sustained levels of active silver ions; microbial resistance is rare; less painful and few adverse effects than silver nitrate; variety of products | Levels of silver ions at wound interface not well defined; may cause silver staining of tissues; may delay epithelialization; relatively expensive; few published comparative trials | $$ | Should not substitute for nonmedicated dressings for uninfected wounds; may be useful for subclinically infected, highly colonized wounds or for wounds being cause pain or lyse blood clots |

FIG 18 (continued)

adaptable to different types of wounds; infrequent application required prepared for skin grafting NOTE. EUSOL, Edinburgh University Solution of Lime; MRSA, methicillin-resistant *S. aureus*; VRE, vancomycin-resistant enterococci.

[a] Costs are approximate in US$ per day for treating 100-cm$^2$ wound, as follows: $, <$3; $$, $3-$15; and $$$, >$15.
[b] US Food and Drug Administration–approval indications.
[c] Available without prescription.

METHOD OF TREATING MULTI-DRUG RESISTANCE BIOFILM USING TARGETED LASER AND ANTIBIOTICS

CROSS-REFERENCE TO RELATED APPLICATIONS

This application claims priority to U.S. Provisional Application No. 62/667,570, filed on May 6, 2018, which is hereby incorporated by reference. This application is a continuation-in-part application of U.S. application Ser. No. 15/974,294 filed on May 8, 2018 (U.S. patent Ser. No. 10/835,755), which is a divisional application of U.S. application Ser. No. 13/900,994 filed on May 23, 2013 (U.S. Pat. No. 9,993,660), which claims the benefit of U.S. Provisional Application No. 61/650,863 filed on May 23, 2012, all of which are hereby incorporated by reference.

GOVERNMENTAL RIGHTS IN THE INVENTION

This invention was made with government support funded by Naval Medical Research Center's Advanced Medical Development Program using work unit number G1025. The research was supported, in part, by an appointment to the Postgraduate Research Participation Program at the Naval Medical Research Unit San Antonio (NAMRU-SA) administered by the Oak Ridge Institute for Science and Education through an interagency agreement between the U.S. Department of Energy and NAMRU-SA. The government has certain rights in the invention.

BACKGROUND

This invention relates to live biofilm targeting and subsequent photothermal and photoacoustic eradication of established biofilm, using gold nanoparticle (GNP)-targeted pulsed laser therapy in combination with administration of antimicrobial agent.

Multi-drug resistant (MDR) pathogens are becoming the most common cause of infectious disease-related deaths around the world, killing more Americans every year than colon and breast cancer combined [1, 2]. The continued emergence of antimicrobial resistance is a growing public health concern because it is quickly outpacing the development of new antibiotics [1, 2] and seriously compromises our ability to treat infections. This problem is exacerbated by the propensity of many bacterial strains to form biofilms, which are present in 65%-80% of human infections [3] and associated with treatment failures in chronic infections, which in turn result in increases in morbidity, mortality, and cost of care [1, 2]. Biofilm-associated bacteria are 100-1,000 times more tolerant to antibiotics and other forms of treatments than planktonic (free-floating) bacteria [4]. This heightened drug tolerance of biofilms is attributed to multiple factors including decreased penetration of antimicrobial agents through the extracellular matrix and reduced metabolic rates of bacteria in underlying, nutrient-deprived regions of the biofilm [5-7]. Currently, the most effective means of treating biofilm-related infections is by elimination of the biofilm's growth surfaces from wound sites using debridement [8, 9] or removal of medical implants such as catheters, artificial hips, and contact lenses [10], which result in delayed wound healing, failure of indwelling medical devices, and increased length of hospital stays and medical costs [2, 4, 8, 23, 24].

The continually evolving challenges associated with treatment of MDR bacterial infections have spawned interest in the development of non-traditional approaches that aim to overcome the antibiotic tolerance, and multi-drug resistance related to biofilms. Fortunately, the recent advancements in nanotechnology research has led to the development of cutting-edge nanoparticle-targeted laser therapies that may overcome these challenges via photothermal and/or photoacoustic destruction of the biofilm matrix and resident bacteria. A notable advantage of this strategy is that it may be effective at eradicating pathogens regardless of their level of antibiotic resistance, growth rate, or metabolic status within biofilms [13]. These potential therapies exploit the unique surface plasmon resonance (SPR) properties of noble metals, particularly gold nanoparticles (GNPs), which strongly absorb energy in the visible light spectrum (104-105 times greater absorption than traditional photoabsorbing dyes), and release the collected energy to the surrounding medium or cells through phonon-phonon interactions [11, 12]. GNPs, convert absorbed photons into thermal energy in the picosecond time scale, causing extremely rapid cell destruction [14]. A notable advantage of this strategy is that it may be effective at eradicating pathogens regardless of their level of antibiotic resistance or metabolic status within biofilms [13]. In addition, GNPs can be utilized for site-specific delivery of laser therapeutics by attachment of targeting agents (e.g., antibodies and aptamers) to the particle surface, thus minimizing collateral damage to healthy tissue [14, 15]. Taken together, these advantages make GNP-targeted laser therapies [17] a great addition to therapy against microbial biofilm and infection, such as those caused by bacteria.

Previous investigations have demonstrated that GNP-targeted laser therapies are capable of destroying drug-resistant bacteria in planktonic and biofilm cultures [16-19] and enhancing the efficacy of antibiotics against biofilms [20]. However, most of these studies employed continuous wave (CW) irradiation with exposure durations, and power densities that may result in bulk sample temperatures of up to ~50-60° C. [20]. A significant limitation of using CW lasers for therapy, therefore, is the build-up of heat in host tissue to levels that exceed the temperature threshold of 47-50° C. for thermal injury [21]. This challenge can possibly be mitigated by using nanosecond (ns)-pulsed laser irradiation, which causes cellular damage via opto-acoustic wave generation and short-duration heating localized to the area near the targeted GNPs (tGNPs) [24]. Zharov et al. demonstrate in vitro bacterial killing using this technique against planktonic (free floating/drifting) *Staphylococcus aureus* cultures, and proposed that the antimicrobial effect was due to generation of opto-acoustic and photothermal phenomena such as intense heating, vapor nanobubbles, and shock waves around the nanoparticles resulting in disruption of bacterial cell walls [13, 22]. The Zharov et al. group subsequently demonstrated the therapeutic potential of using Gold nanoparticle for eliminating *S. aureus* after injection of planktonic cells into blood and tissue using a murine model [22].

The applicant's previous work (U.S. Pat. No. 9,993,660), discloses a different antibody coated gold nanoparticle, which may be used in reduction and prevention of biofilm formation and treatment of wound. The '660 patent further disclosed that one or more antimicrobial agents, such as antibiotics, may also be administered in combination with GNP-targeted laser irradiation. Examples of antimicrobial agents include: a) Chitosan, which is a naturally occurring biopolymer with good biocompatibility and antimicrobial activity against a wide range of bacteria, b) Endopeptidase lysostaphin, which can enzymatically attack the bacterial cell wall; c) dispersin B, which breaks down the extracellular matrix of biofilms, d) and antimicrobial peptides, such as LL-37 and ranalexin that weaken the bacterial membrane or cell wall.

This invention is an extension of the applicant's previous study, and is directed to a method of treating wound infection or eradicating biofilm using GNP-targeted ns-pulsed laser therapy in combination with antimicrobial agents.

DETAILED DESCRIPTION OF DRAWINGS

FIG. 1 Schematic illustration of the methodology used to achieve biofilm dispersal. Spherical gold nanoparticles (GNPs, 40 nm) are coated with antibodies against MRSA or *P. aeruginosa*, which enable specific adhesion of GNPs to the biofilm. Biofilms pre-treated with antibody-targeted GNPs are subjected to ns-pulsed laser irradiation at 532 nm. GNPs rapidly absorb and amplify local laser energy delivery, creating thermal energy and acoustic waves to disperse the biofilms.

Figure 2:
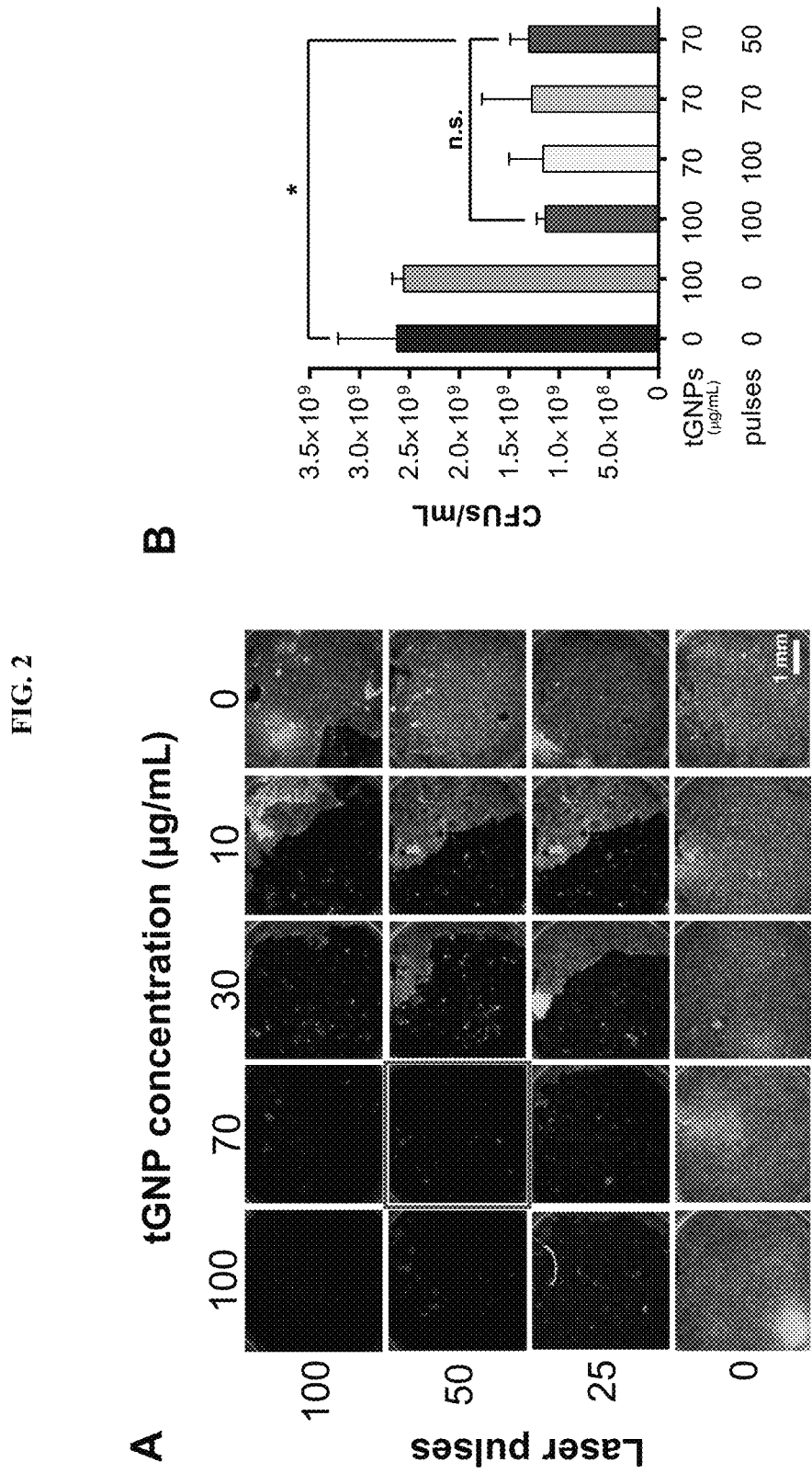

FIG. 2 Determination of laser dosage and tGNP concentration for optimal MRSA biofilm dispersion. (A) Confocal micrographs of MRSA biofilms stained with Con-A and DAPI and (B) viability of MRSA biofilms following treatment with varied concentrations of tGNPs and numbers of laser pulses indicating optimal dispersion of biofilms after treatment with 70 µg/mL of tGNPs and 50 laser pulses. Representative micrographs from two independent experiments are shown. *$p=0.01$ compared to controls for $n=3$ with three replicate samples per experimental condition; n.s. denotes no significance.

Figure 3:
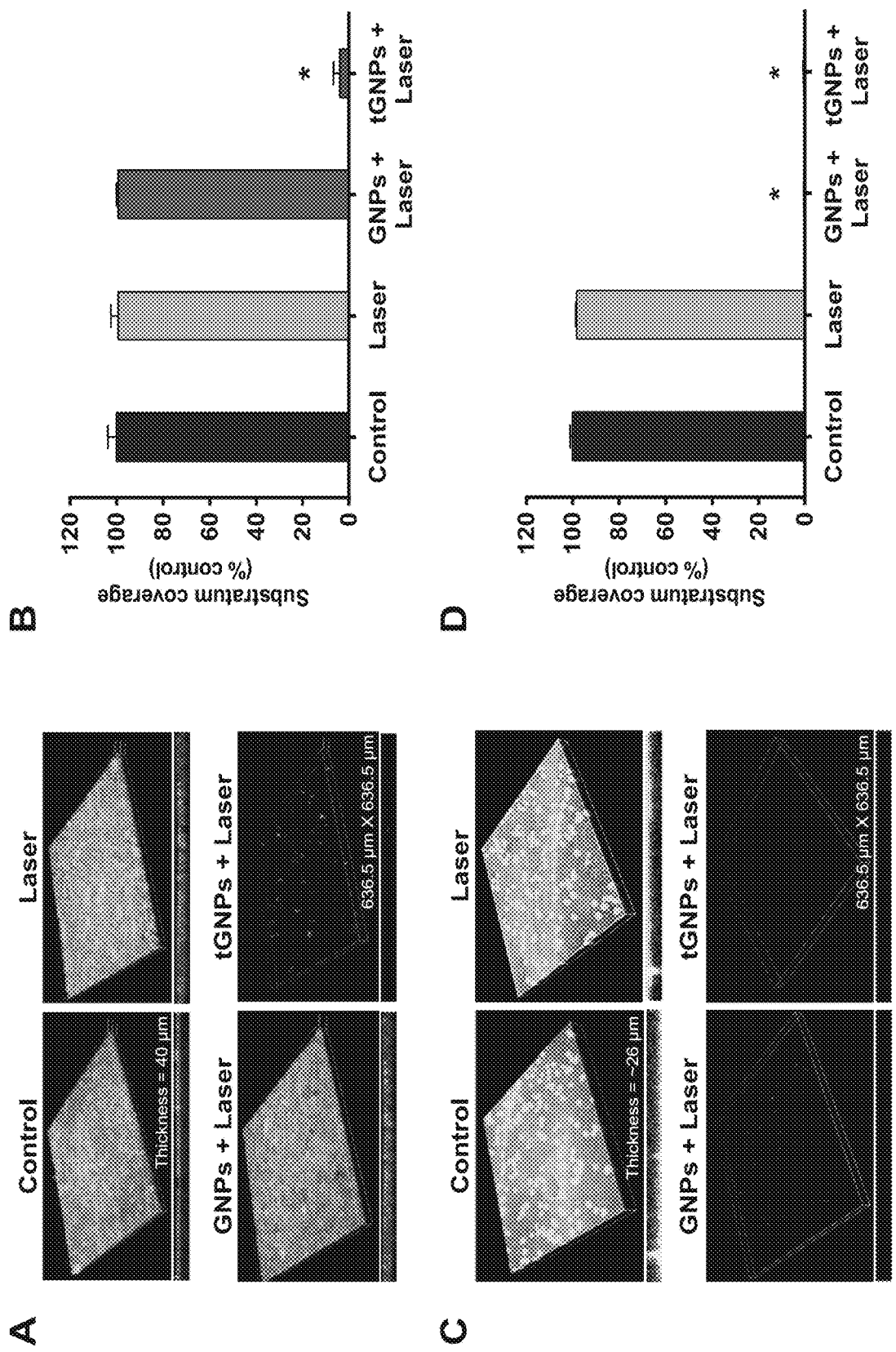

FIG. 3 Comparison of targeted and non-targeted GNPs for use in laser therapy. (A) Confocal micrographs showing targeted dispersion of MRSA biofilms after treatment with tGNPs plus laser, but no dispersion after treatment with non-targeted GNPs plus laser or laser alone. (B) ImageJ® analysis of the confocal micrographs confirmed tGNPs plus laser irradiation caused significant dispersion of MRSA biofilms. *$p<0.0001$ compared to controls ($n=3$). (C) Confocal micrographs showing dispersion of *P. aeruginosa* biofilms after treatment with non-targeted GNPs plus laser or tGNPs plus laser, but no dispersion in samples treated with laser alone. (D) Image J® analysis of the confocal micrographs confirmed that treatment with non-targeted GNPs plus laser or tGNPs plus laser caused significant dispersion of *P. aeruginosa* biofilms. *$p<0.0001$ compared to controls ($n=4$). Images of dispersed biofilms are from the central damage zone, i.e., presumed site of highest pulse energy deposition.

Figure 4:
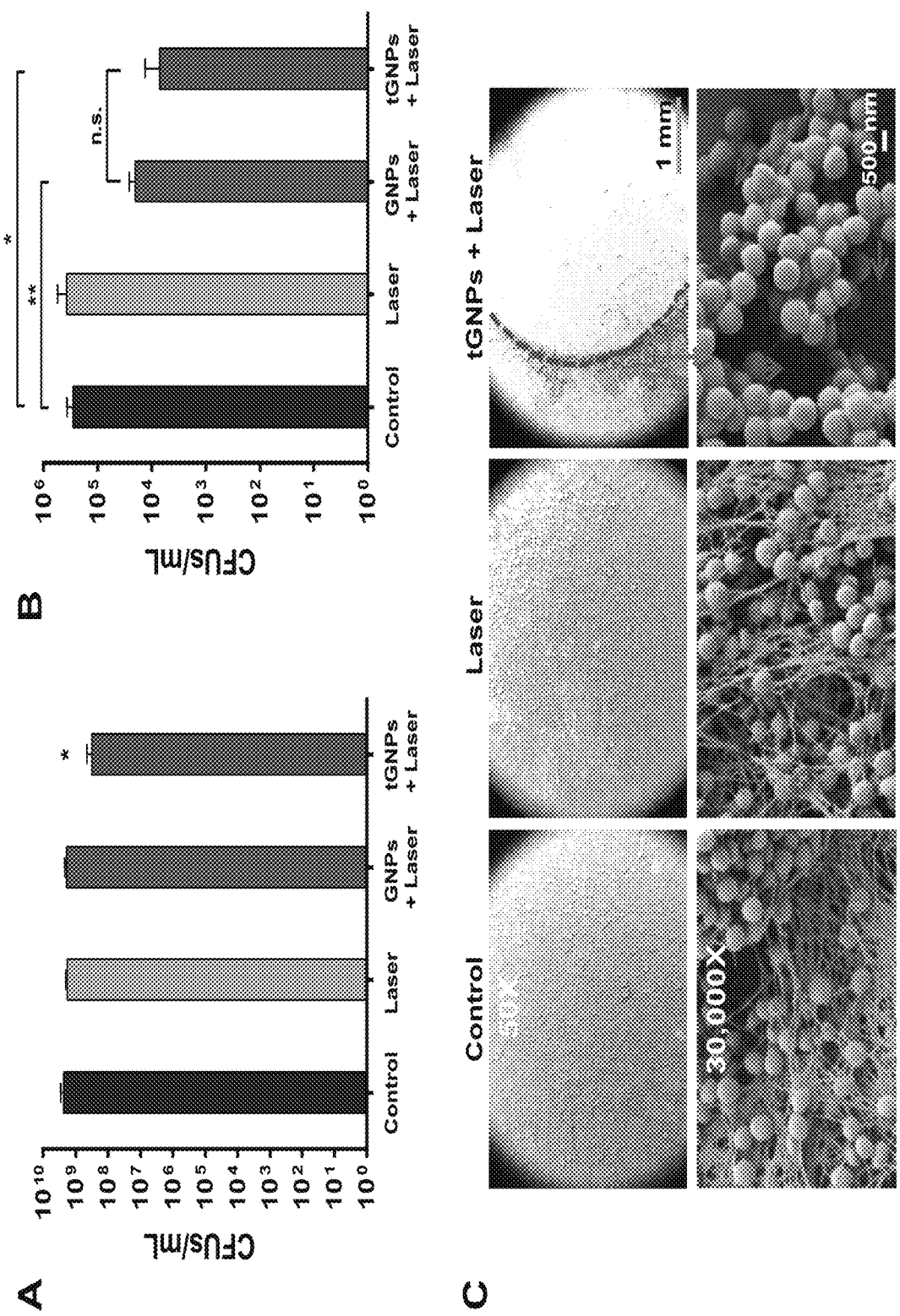

FIG. 4. GNP-targeted laser therapy caused significant cell killing and morphology changes in biofims. (A) CFU assays showed treatment with tGNPs plus laser led to ~1-log reduction in MRSA biofilm viability relative to controls. *$p=0.007$ compared to controls forn=3 with three replicate samples per experimental condition. (B) CFU assays showed treatment with tGNPs plus laser or bare GNPs plus laser caused ~1-log reduction in *P. aeruginosa* biofilm viability compared to untreated controls. *$p=0.006$ and **$p<0.0001$ for $n=5$ with three replicate samples per experimental condition; n.s. denotes no significance. (C) SEM images of MRSA biofilms showing targeted dispersion of biofilms following treatment with tGNPs and laser irradiation. The dashed red line indicates the boundary between the damage zone caused by the laser beam and residual biofilm. Red arrows indicate areas of cell and matrix detachment in the residual biofilm. Controls and samples treated with laser alone showed no discernable biofilm dispersion (no clear zone).

Figure 5:
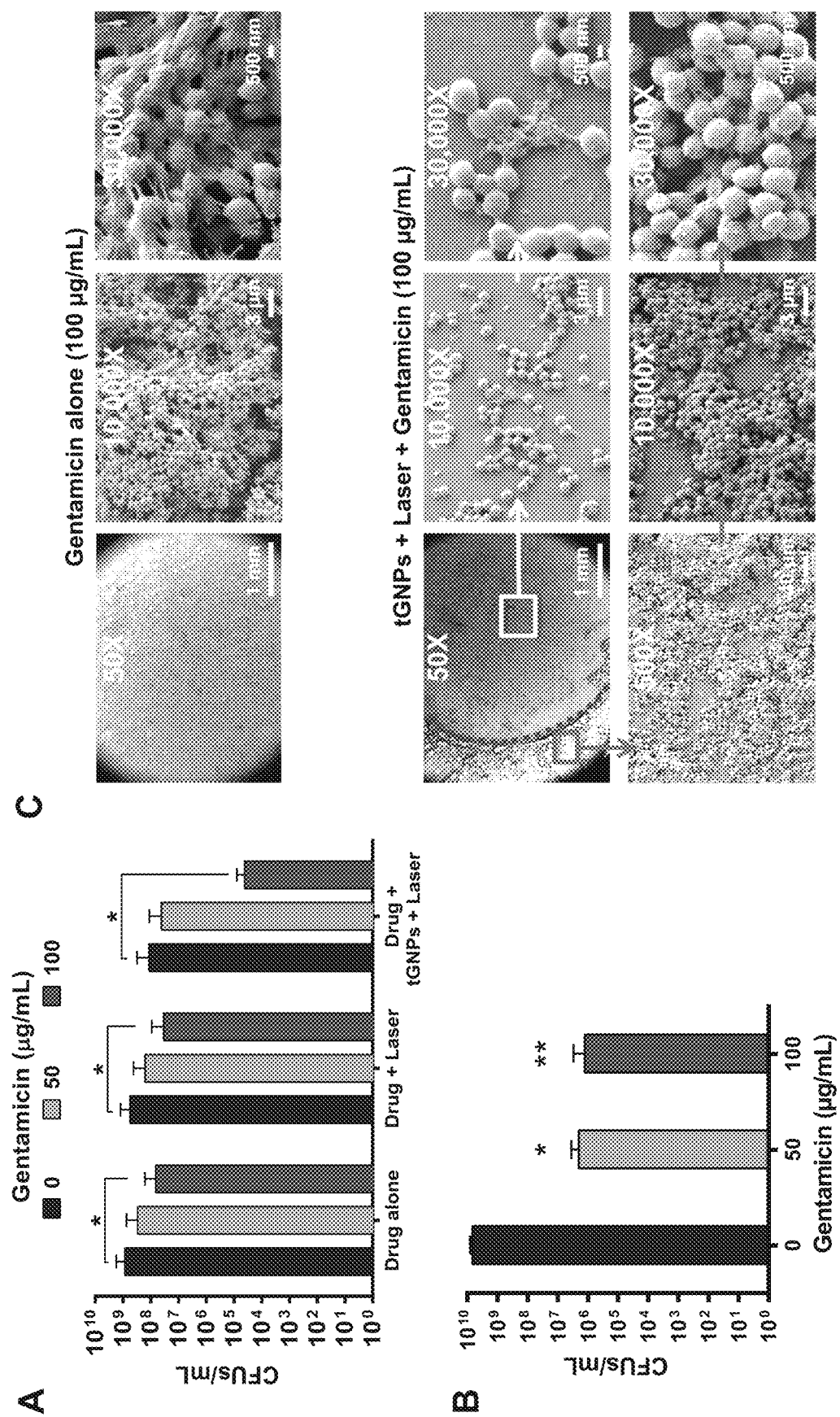

FIG. 5. Synergistic enhancement of gentamicin effect against MRSA biofims by GNP-targeted laser therapy. (A) CFU assays showed treatment with GNP-targeted laser therapy plus gentamicin at 100 µg/mL caused a 4-log reduction in MRSA biofilm viability, whereas treatment with gentamicin or GNP-targeted laser alone achieved only a 1-log reduction in viability relative to controls. *$p<0.03$ for $n=4$ with three replicate samples per experimental condition. (B) CFU assays showed gentamicin caused a 4-log reduction in the viability of planktonic MRSA cultures compared to controls. *$p=0.003$ and **$p=0.01$ compared to controls ($n=3$). (C) SEM images confirmed that GNP-targeted laser therapy dispersed MRSA biofilms (dashed red line indicates boundary of damage zone caused by the laser beam) and biofilms treated with gentamicin alone showed no apparent dispersion.

Figure 6:
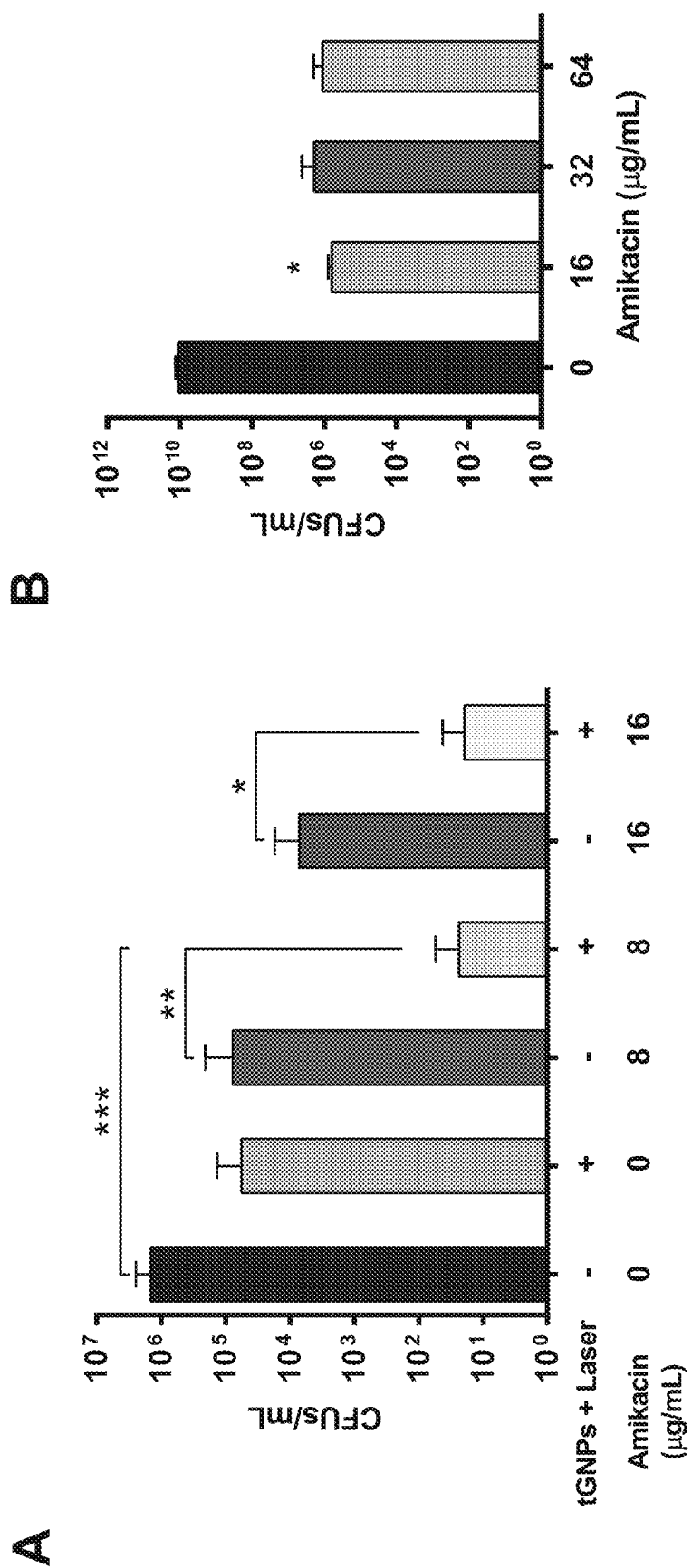

FIG. 6. GNP-targeted laser therapy synergized with amikacin against *P. aeruginosa* biofilms. (A) Biofilms treated with GNP-targeted laser therapy and amikacin exhibited a 5-log reduction in bacterial viability, whereas amikacin at 8 µg/mL or GNP-targeted laser therapy alone caused only ~1-log reduction in viability relative to controls. *$p=0.006$, $p=0.0003$, and *$p=0.0001$ ($n=5$). (B) A 24-h treatment of planktonic *P. aeruginosa* cultures with amikacin led to a 4-log reduction in viability relative to controls. *$p<0.0001$ compared to controls ($n=3$).

Figure 7:
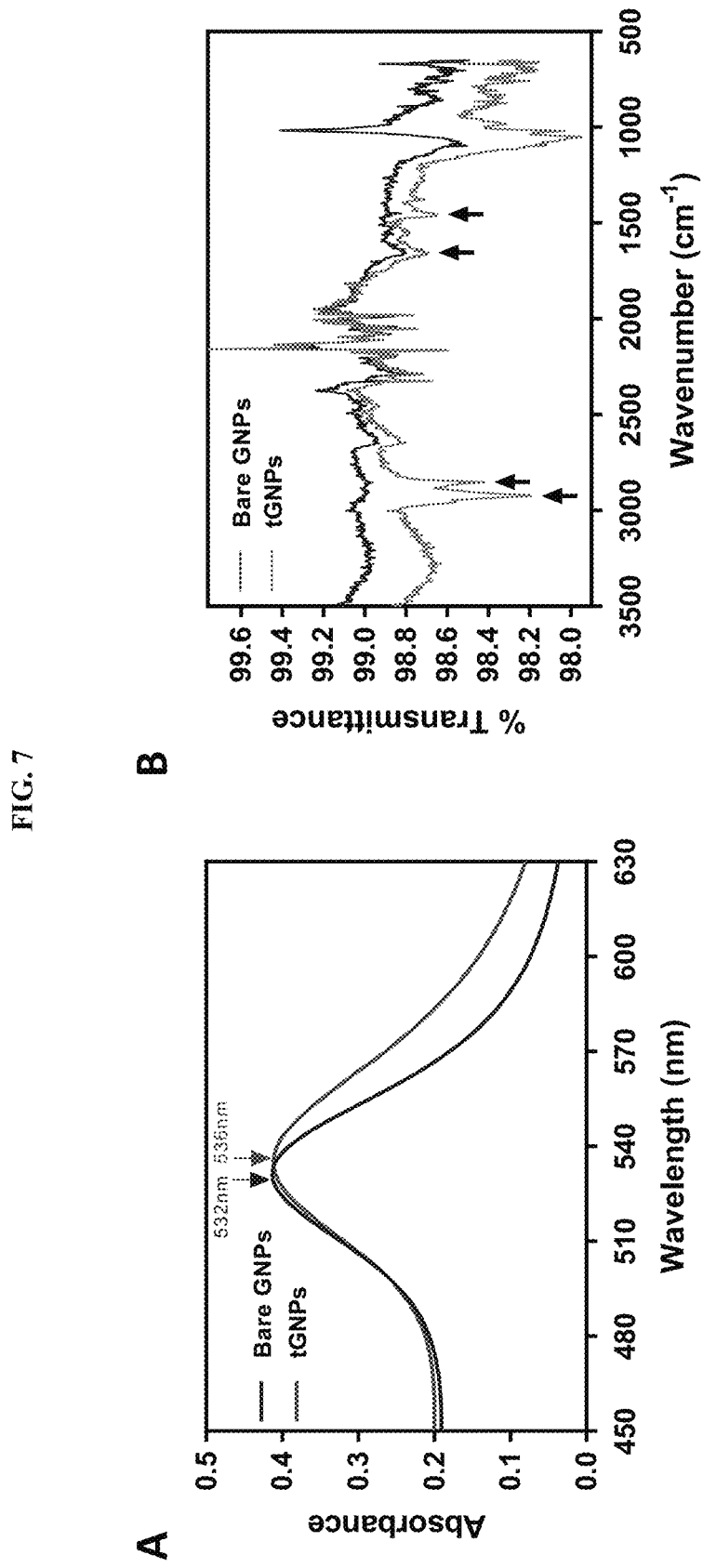

FIG. 7. Characterization of tGNPs using UV-Vis and FTIR spectroscopy to confirm antibody attachment. (A) UV-Vis absorption spectra of non-conjugated (bare) GNPs and GNPs conjugated to anti-*S. aureus* antibodies (tGNPs) showed a 4-nm "red-shift" from 532 to 536 nm that indicates successful attachment of molecules to the GNP surface. (B) FTIR scans of non-conjugated GNPs and tGNPs revealed distinct peaks at 2971 and 2850 $cm^{-1}$ for CHz stretching, a peak at 1721 $cm^{-1}$ for C=O stretching, and a peak at 1485 $cm^{-1}$ associated with CH scissoring, which are denoted with arrows. These signature peaks indicate the presence of antibodies on the GNPs. UV-Vis and FTIR spectra for GNPs conjugated to anti-*P. aeruginosa* antibodies showed similar results (data not shown).

Figure 8:
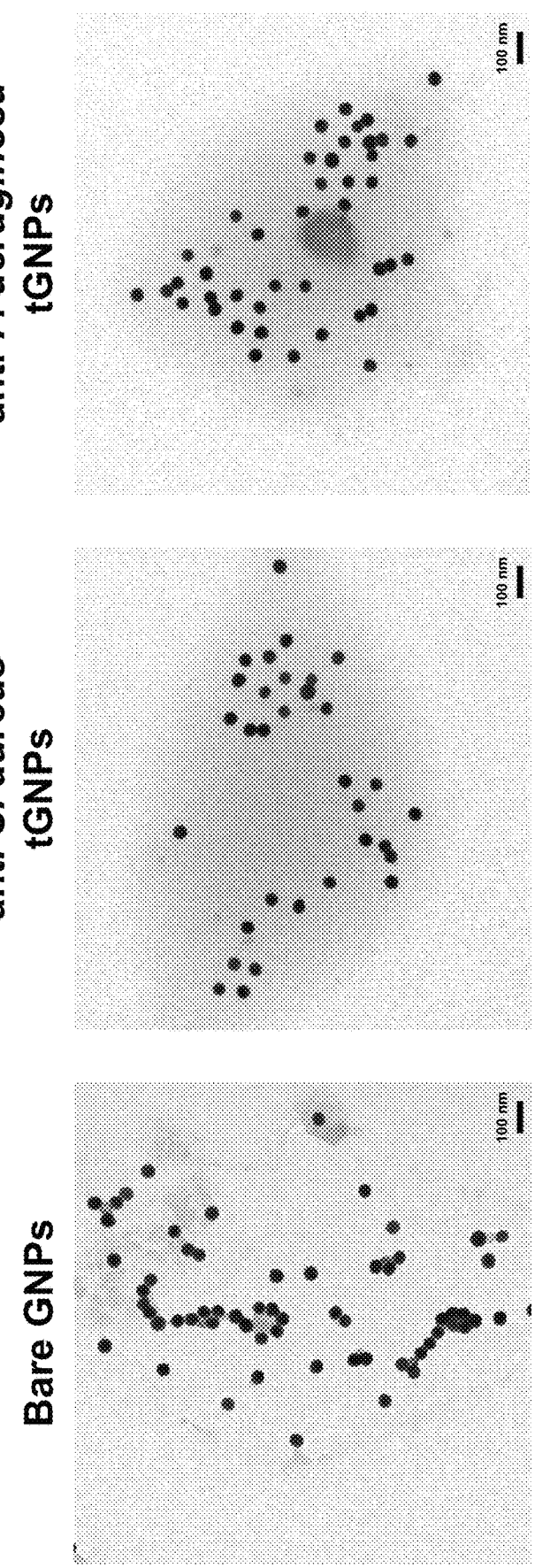

FIG. 8 Transmission electron microscope (TEM) images showing 40-nm GNPs before and after antibody conjugation. Micrographs revealed that the tGNPs exhibit good dispersion after conjugation to antibodies against *S. aureus* or *P. aeruginosa*. Images were captured at 100,000× magnification using a JEOL 1400 TEM (JEOL USA, Inc., Peabody Mass.).

Figure 9:
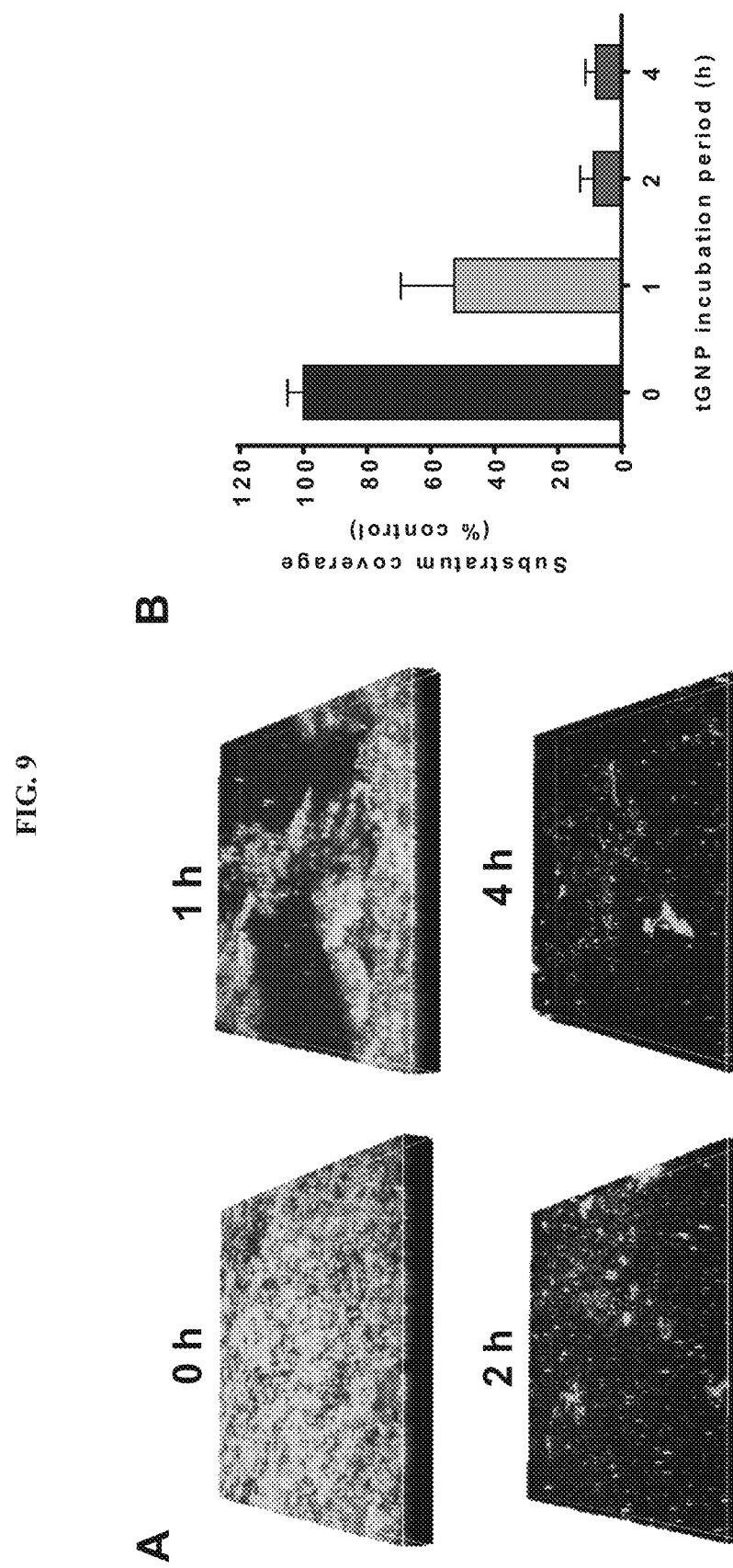

FIG. 9 Determination of tGNP treatment duration for optimal MRSA biofilm dispersion. (A) Representative confocal micrographs of MRSA SA5120 biofilms incubated with 70 µg/mL of tGNPs for 0, 1, 2, or 4 h; treated with 50 laser pulses; and then stained with Con-A and DAPI. Micrographs revealed that a 2-h tGNP incubation period prior to laser irradiation was sufficient to cause substantial biofilm dispersion compared to controls. (B) ImageJ® analysis of the confocal micrographs confirmed the optimal duration of tGNP incubation to be 2 h, which led to dispersion of 91±4% of biofilms relative to controls. Data from two independent experiments with three replicates per experimental condition are shown.

Figure 10:
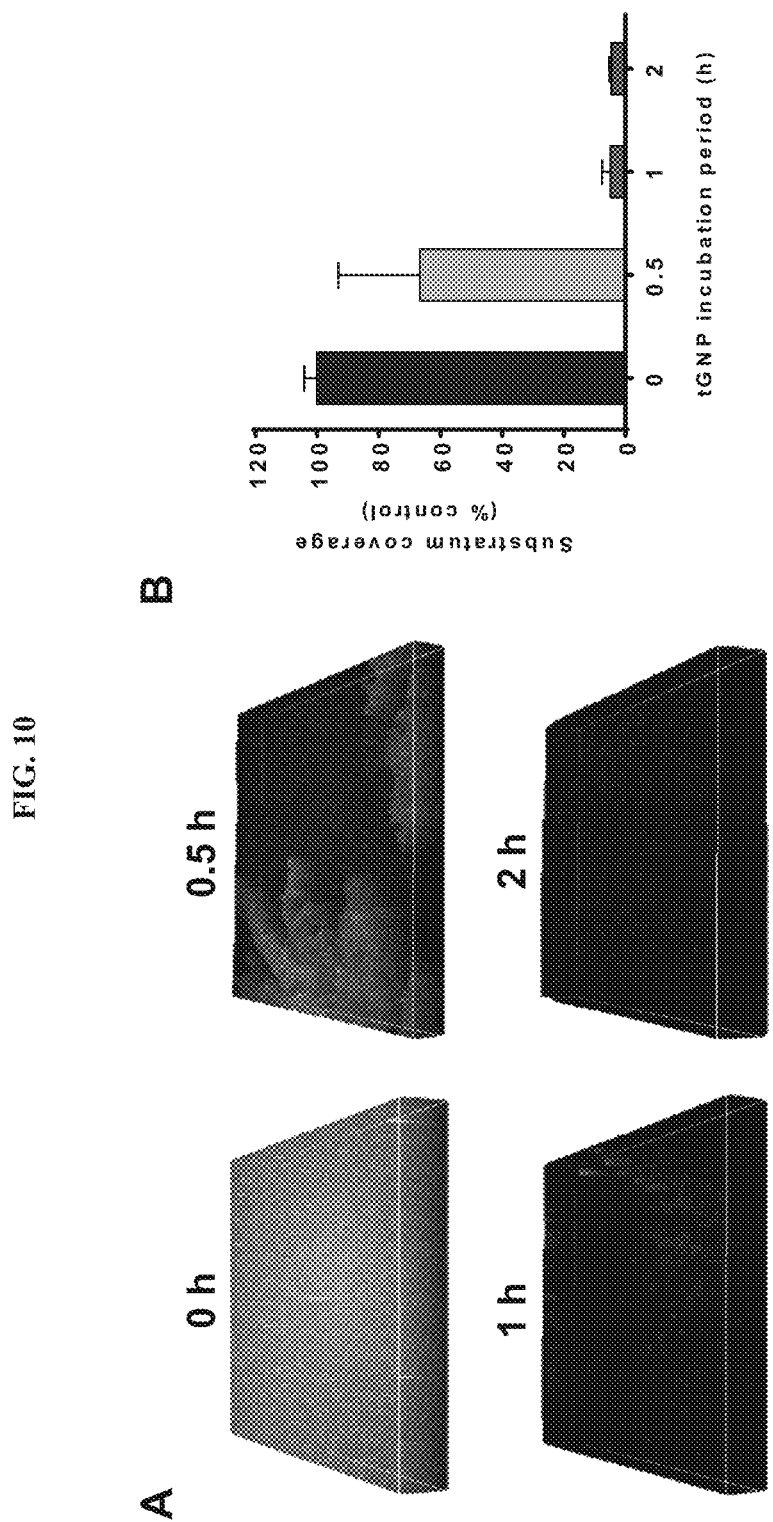

FIG. 10. Determination of tGNP treatment duration for optimal *P. aeruginosa* biofilm dispersion. (A) Representative confocal micrographs of *P. aeruginosa* PA 60-65 biofilms incubated with 70 µg/mL of tGNPs for 0, 0.5, 1, or 2 h; treated with 50 laser pulses; and then stained with Con-A and DAPI. Micrographs revealed that a 1-h tGNP incubation period prior to laser irradiation was sufficient to cause extensive dispersion of biofilms compared to untreated controls. (B) ImageJ® analysis of the confocal micrographs confirmed that the optimal duration of tGNP incubation was 1 h, which led to dispersion of 95.1±3% of biofilms relative to controls. Data from two independent experiments with three replicates per experimental condition are shown.

Figure 11:
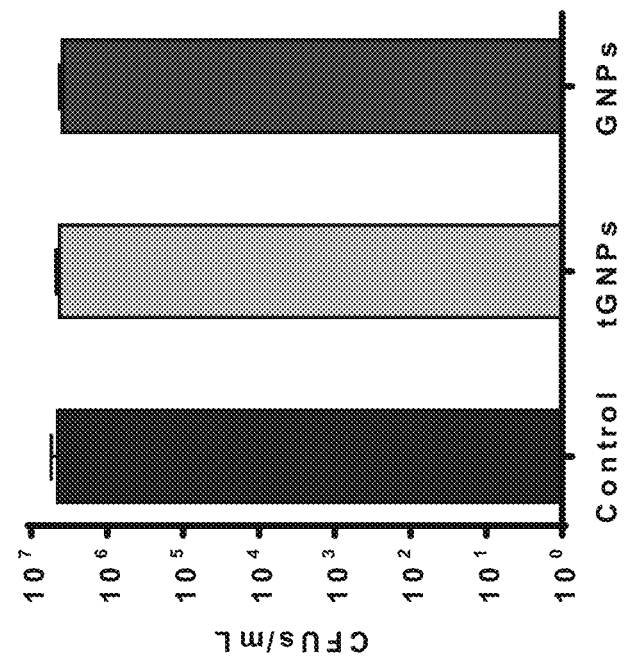
Figure 11:
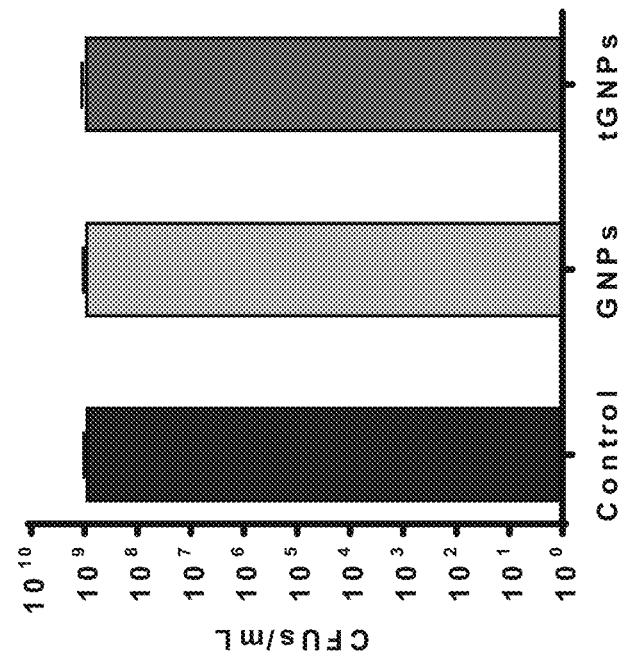

FIG. 11. Treatment of (A) & aureus and (B) P. aeruginosa biofims with bare GNPs or tGNPs did not reduce bacterial viability. Biofilms grown on glass discs were treated with PBS alone as controls or with 70 µg/mL of GNPs or tGNPs for 2 h (S. aureus SA5120) or 1 h (P. aeruginosa PA 60-65) and subsequently incubated with 100 µg/mL of papain (S. aureus) or 0.0225 U/mL of β-mannosidase (P. aeruginosa) to loosen the biofilms. CFU assays showed no reduction in viability of biofilms treated with bare GNPs or tGNPs relative to controls. Data from two independent experiments with three replicates per experimental condition are shown for each organism.

Figure 12:
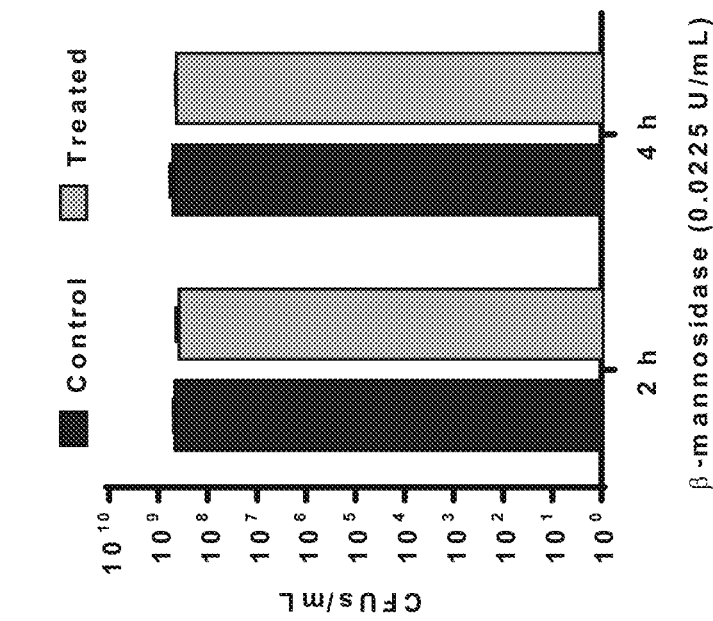
Figure 12:
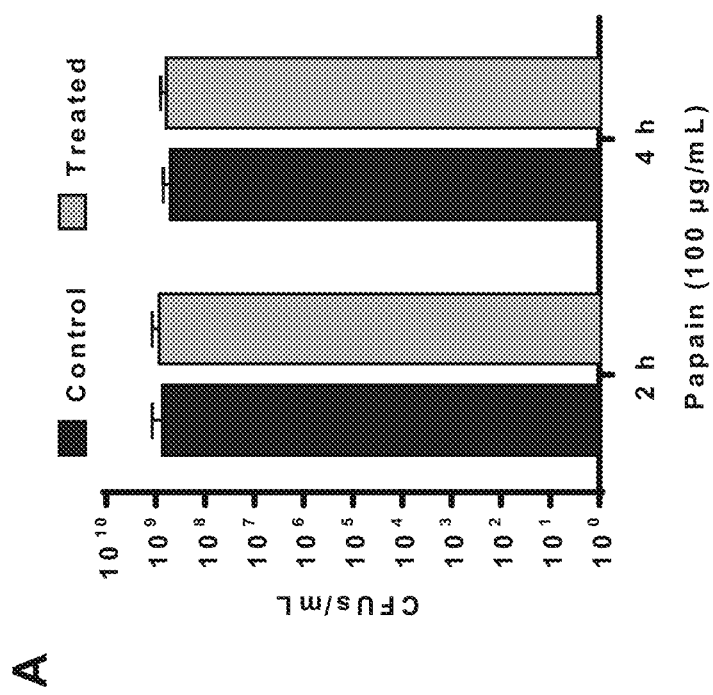

FIG. 12. Cell viability assays revealed that treatment of planktonic cultures with papain or β-mannosidase did not reduce bacterial viability. CFU assays showed treatment of (A) planktonic MRSA cultures with 100 µg/mL of papain or (B) planktonic P. aeruginosa cultures with 0.0225 U/mL of β-mannosidase for 2 or 4 h at 37° C. caused no reduction in cell viability (n=3). Data confirmed that use of these enzymes to disrupt biofilms prior to CFU assay analysis would not cause bacterial cell death.

Figure 13:
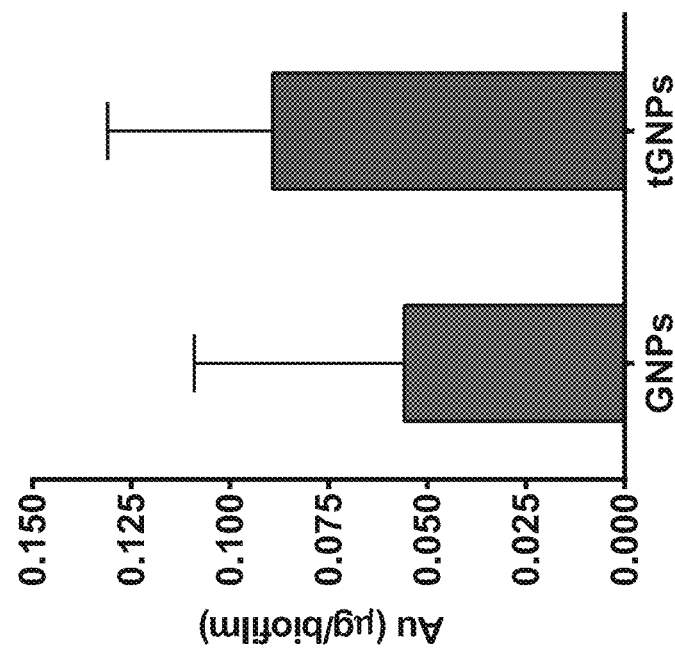
Figure 13:
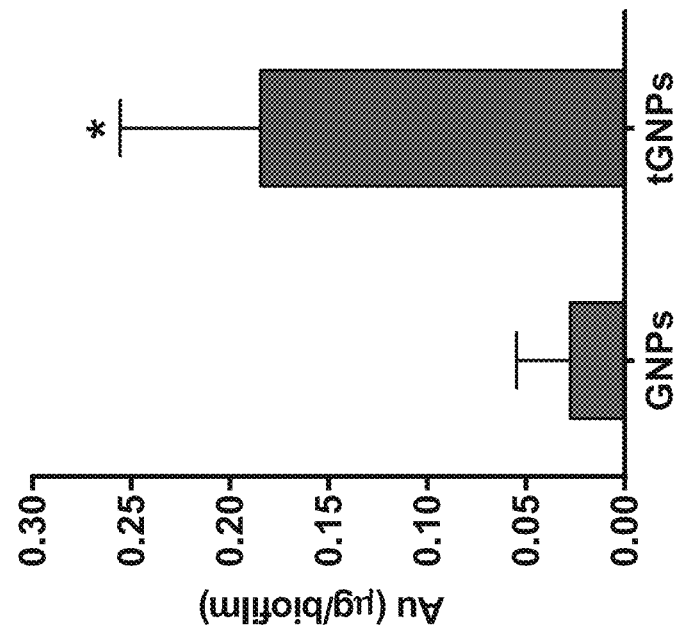

FIG. 13. ICP-MS analysis of amount of bare GNPs and tGNPs that bound to (A) S. aureus and (B) P. aeruginosa biofilms. *p<0.05 for bare GNPs compared to tGNPs as determined using a t-test with n=4.

Figure 14:
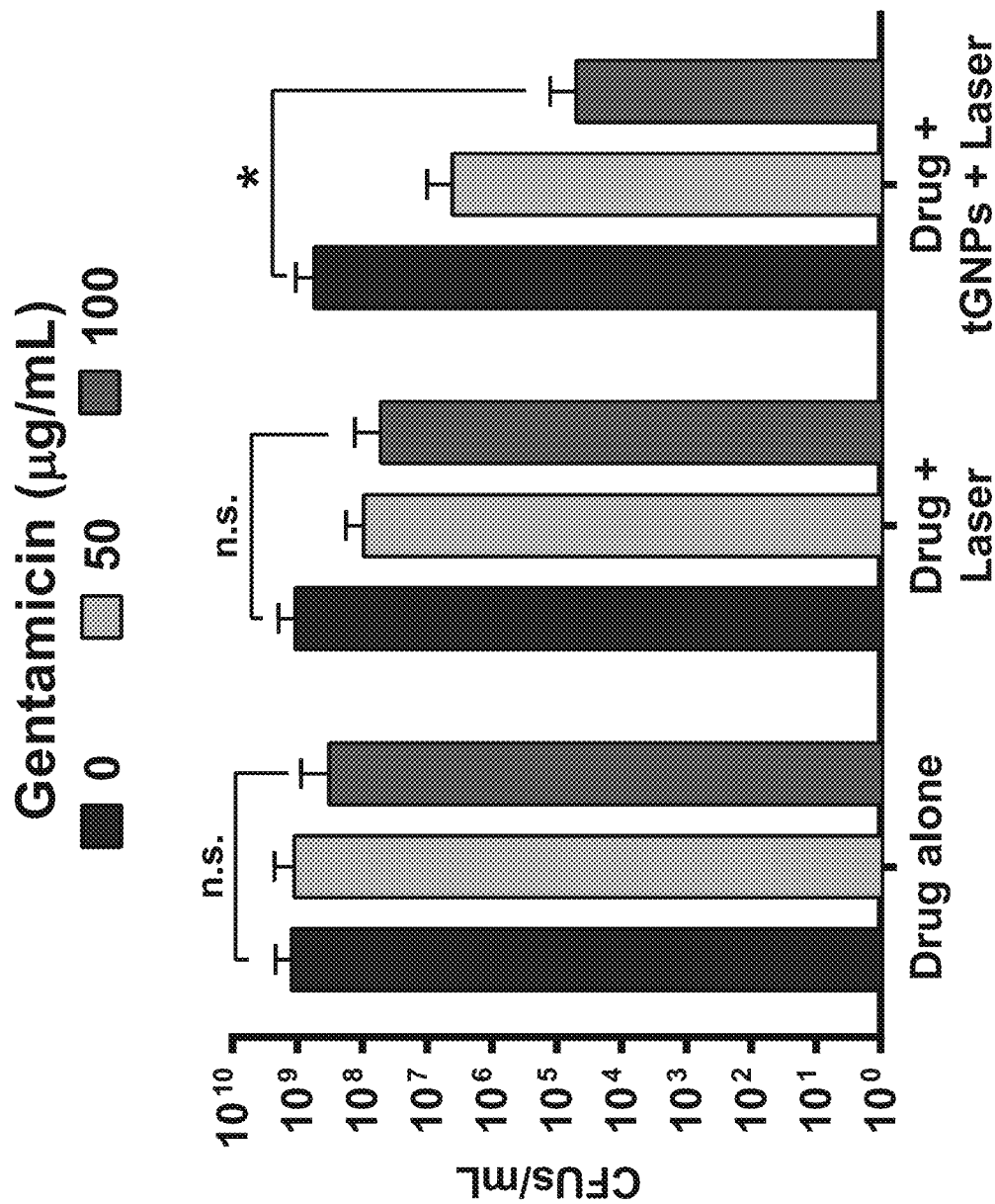

FIG. 14. Cell viability assay results for combination of GNP-targeted laser therapy and 48-h gentamicin treatment. CFU assays revealed that no additional therapeutic benefit was achieved by treating MRSA biofilms with gentamicin for 48 h instead of 24 h (see FIG. 5) following GNP-targeted laser therapy. *p<0.05 (n=3); n.s. denotes no significance.

Figure 15:
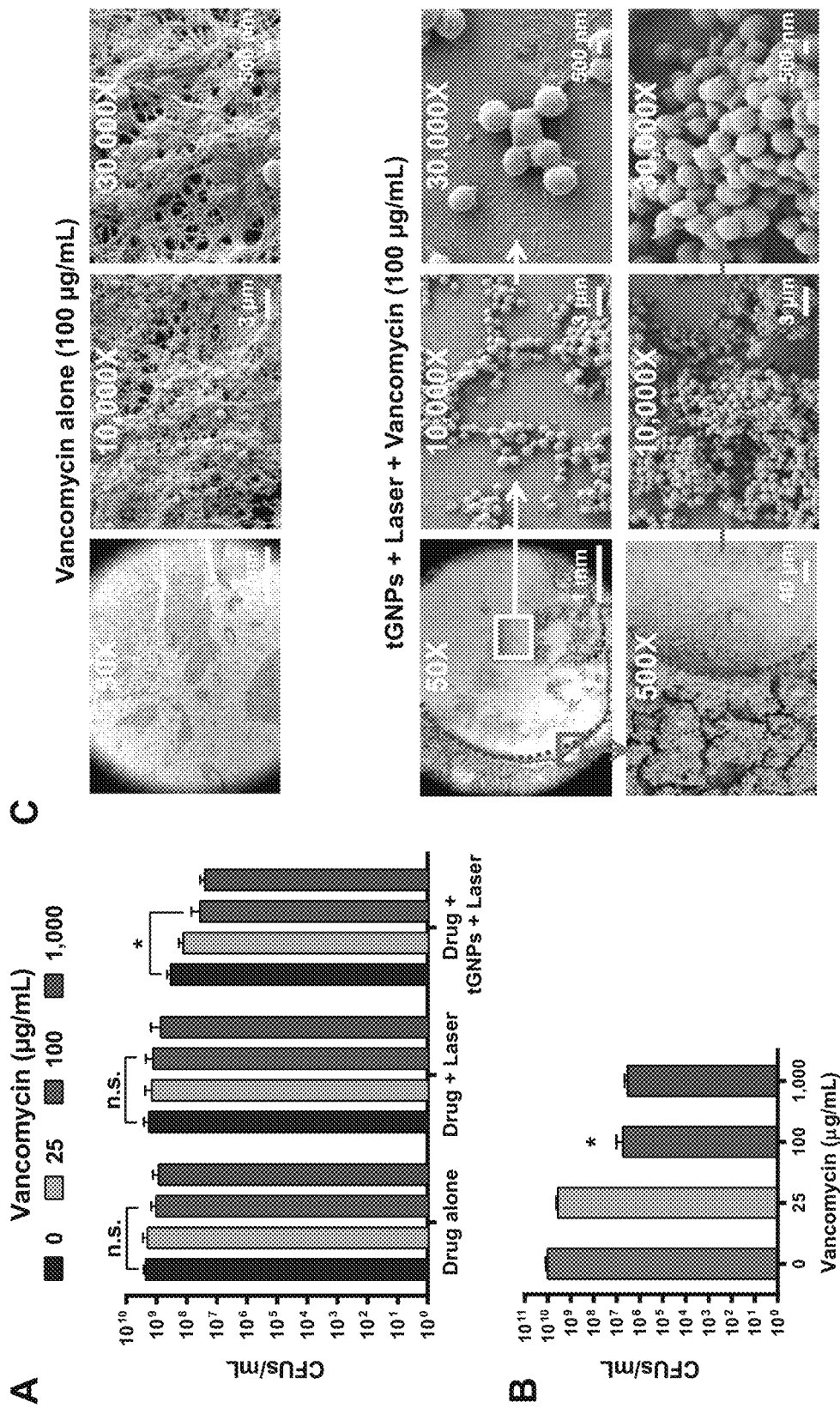

FIG. 15. GNP-targeted laser therapy enhanced the efficacy of vancomycin against MRSA biofims. (A) GNP-targeted laser therapy plus vancomycin at 100 µg/mL led to a 2-log reduction in CFUs/mL, whereas vancomycin or GNP-targeted laser treatment alone caused <1-log reduction in biofilm viability relative to controls. *p=0.006 (n=4); n.s. denotes no significance. (B) Planktonic MRSA cultures treated with 100 µg/mL of vancomycin showed ~3-log reduction in viability. *p=0.003 compared to controls (n=3). (C) SEM images showed GNP-targeted laser therapy dispersed biofilms; the dashed red line indicates the boundary of the damage zone caused by the laser beam. Treatment with vancomycin alone (top row of images) appeared to thicken the biofilm matrix compared to the untreated control biofilms shown in FIG. 4C. This is a possible explanation for the reduced efficacy of vancomycin compared to gentamicin against MRSA biofilms when used in combination with GNP-targeted laser therapy.

Figure 16:
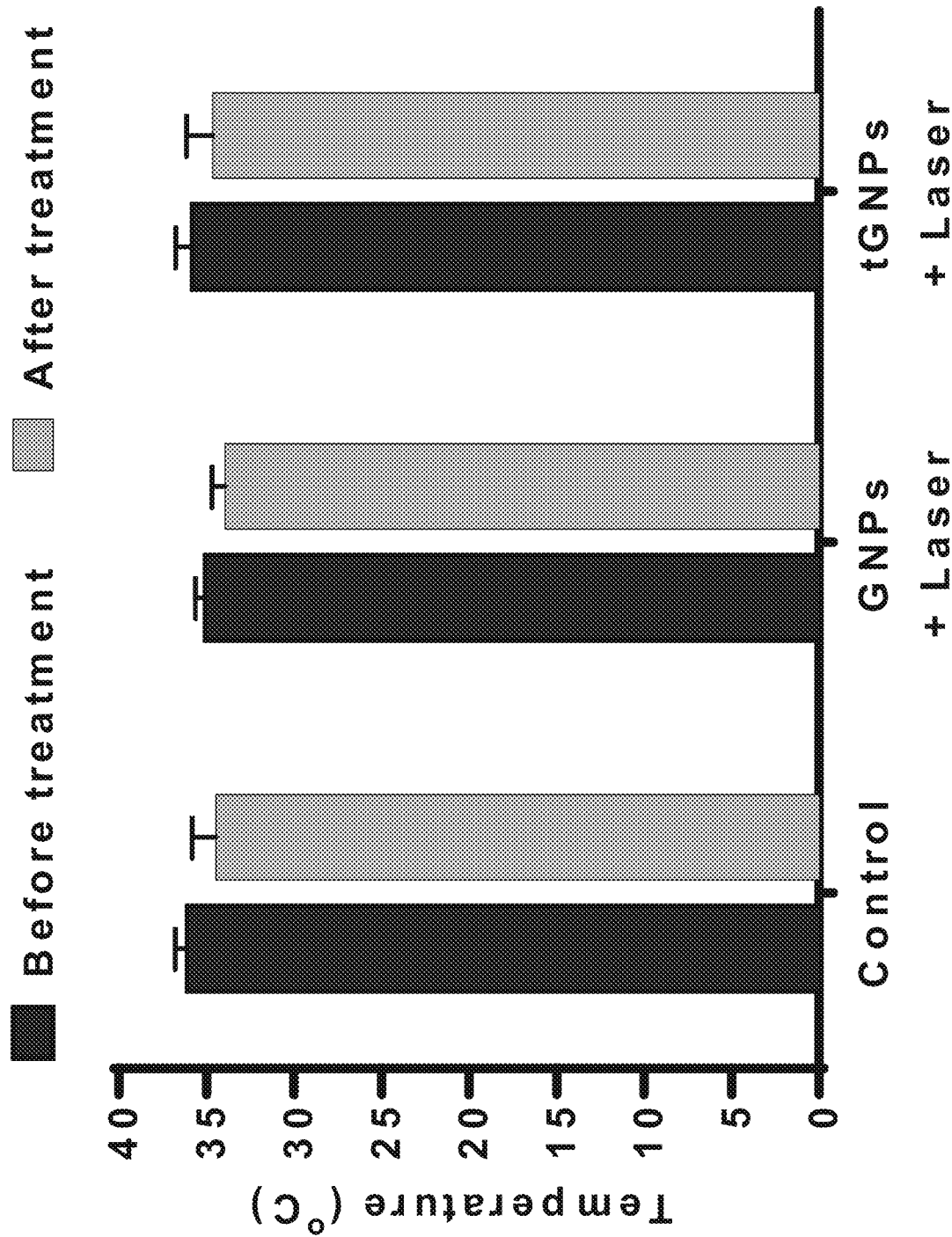

FIG. 16. Temperature measurements revealed that treatment of & aureus biofilms with bare GNPs or tGNPs plus laser irradiation did not cause bulk sample heating. S. aureus biofilms grown on glass discs were treated with 70 µg/mL of GNPs or tGNPs for 2 h, samples were rinsed with PBS, and 40 µL of PBS was added to each well of the 96-well sample plate. A thermocouple wire (5TC-TT-T-30-36, OMEGA, Norwalk, Conn.) placed close to the top of the biofilm and a data logger (OM-DAQPRO-5300, OMEGA) were used to acquire temperature readings immediately before and after treatment of samples with 50 laser pulses (532 nm, ~1 J/cm$^{-2}$). Temperatures were also obtained from sham-exposed controls. No significant increase in temperature was detected in any of the samples after laser exposure, but rather a slight reduction was observed due to equilibration of samples with the ambient temperature. Data are representative of two independent experiments with three replicates per experimental condition.

FIG. 17 shows Table 2: topical Antibiotic Products Available for Treating Chronic Wounds FIG. 18 shows Table 3: Topical Antiseptic Products Available for Treating Chronic Wounds

DETAILED DESCRIPTION OF THE INVENTION

Definitions

Unless defined otherwise herein, all technical and scientific terms used herein have the same meaning as commonly understood by one of ordinary skill in the art. Singleton, et al., *Dictionary of Microbiology and Molecular Biology*, third ed., John is Wiley and Sons, New York (1994), and Hale & Markham, *The Harper Collins Dictionary of Biology*, Harper Perennial, N.Y. (1991) provide one of skill with a general dictionary of many of the terms used in this invention. Any methods and materials similar or equivalent to those described herein can be used in the practice or testing of the present invention.

The term "microbiological film" or "biofilm", refers to any group of microorganisms in which cells stick to each other, and often these cells adhere to a surface to form a thin film. These adherent cells may be frequently embedded within a self-produced matrix of extracellular polymeric substance (EPS). A biofilm further includes water and may include other trapped particles. A biofilm may include one or more microorganisms, including gram-positive or gram-negative bacteria (aerobic or anaerobic), algae, protozoa, and/or yeast or filamentous fungi. In some embodiments, the biofilm includes living cells of bacterial genera of *Staphylococcus, Streptomyces, Pseudomonas, Listeria, Streptococcus,* and *Escherichia.*

The term "altering and/or disrupting" of a microbiological films, refers to altering the density of the biofilm, e.g. decreases the density of the microbiological film or increases the space between the cells without releasing cells from the biofilm or where one at least partially or completely disrupts the film.

The term "acute wound" as used herein refers to a wound that heals in a short amount of time Examples of acute wounds include, but are not limited to partial-thickness burn, laceration, bullet wound or infected wound.

The term "chronic wound" as used herein refers to wounds that take a long time to heal or that do not heal without external intervention. Yet further, as used herein, a "chronic wound". also referred to as "chronic ulcer" can be broadly classified into three major types. diabetic ulcers, venous stasis ulcers, decubitus or pressure ulcers. Still further, a chronic wound can also include infected wounds that take a long time to heal.

The term "administration" or "administering" refers to a method of giving a dosage of a composition or pharmaceutical composition to a vertebrate, where the method is by any route, e.g., intrarespiratory, nasal, topical, intravenous, intraperitoneal, intramuscular, transmucosal, buccal, rectal, vaginal, or sublingual. The preferred method of administration can vary depending on various factors, e.g., the components of the pharmaceutical composition, the site of the disease, the disease involved, and the severity of the disease.

The term "pharmaceutically acceptable carrier" or "pharmaceutically acceptable excipient" includes any and all solvents, dispersion media, coatings. The use of such media and agents for pharmaceutically active substances is well known in the art. Except insofar as any conventional media or agent is incompatible with the active ingredients, its use in the therapeutic compositions is contemplated. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (2006); Goodman and Gilman's: The Pharmacological Basis of Therapeutics, 11th Ed., The McGraw-Hill Companies.

"Subject" or "patient" or "individual" as used herein, means a human or a non-human mammal, e.g., a dog, a cat, a mouse, a rat, a cow, a sheep, a pig, a goat, a non-human primate or a bird, e.g., a chicken, as well as any other vertebrate.

A therapeutic effect relieves, to some extent, one or more of the symptoms of the disease, and includes curing a disease. "Curing" means that the symptoms of active disease are eliminated. However, certain long-term or permanent effects of the disease may exist even after a cure is obtained (such as tissue damage).

"Treat," "treatment," or "treating," as used herein refers to administering a pharmaceutical composition or procedure for therapeutic purposes. The term "therapeutic treatment" refers to administering treatment to a patient already suffering from a disease thus causing a therapeutically beneficial effect, such as ameliorating existing symptoms, preventing additional symptoms, ameliorating or preventing the underlying metabolic causes of symptoms, postponing or preventing the further development of a disorder and/or reducing the severity of symptoms that will or are expected to develop.

The term "Eradication" of a biofilm refers to reduction or elimination of biofilm from a surface, including killing and/or inhibition of growth of microbes in the biofilm, and/or prophylactic prevention of formation of or growth of a biofilm on a surface.

In general, an "effective amount" of a biologically and/or pharmacologically active agent is an amount sufficient to achieve a desired biological and/or pharmacological effect when delivered to a cell or organism according to a selected administration form, route, and/or schedule. As will be appreciated by those of ordinary skill in this art, the absolute amount of a particular agent that is effective may vary depending on such factors as the desired biological endpoint, the agent to be delivered, the target tissue, etc Those of ordinary skill in the art will further understand that an "effective amount" may be administered in a single dose, or may be achieved by administration of multiple doses. For example, an effective amount of an antibiotic agent may be an amount sufficient to achieve one or more of the following: (i) inhibit microbial growth in culture or in vivo; (ii) reduce the severity of or prevent one or more symptoms or signs of an infection, (iii) significantly reduce the risk of recurrence of an infection; (iv) significantly reduce the risk of a clinically significant infection in a subject who has been exposed to an infectious agent, etc.

The term "antimicrobial agents" refers to drugs, chemicals, or other substances that either kill microorganisms or suppressing their multiplication or growth of microorganisms. Among the antimicrobial agents are antibacterial drugs, antifungal agents, and antiparasitic drugs.

The present invention will be described with respect to particular embodiments and with reference to certain drawings but the invention is not limited to these embodiments and drawings.

In a first aspect, the present invention relates to a method for treating a wound infection in a subject. The method comprises introducing a composition into a wound, said composition comprising nanoparticles having an electron density that can couple with a photon wave of electromagnetic radiation, wherein said nanoparticles are capable of binding to one or more target microorganisms. The wound is then irradiating by electromagnetic radiation, such as a pulsed laser. The present method also comprises the administration one or more therapeutic effective dose of an antimicrobial agent to said wound or said subject.

According to embodiments of the present invention, the target microorganism may be an aerobic and facultative or anaerobic microorganism known to associates with wound infection. Table 1 shows aerobic and anaerobic isolates identified from acute and chronic wounds of varied etiology.

TABLE 1

AEROBIC AND ANAEROBIC ISOLATES FROM ACUTE AND CHRONIC WOUNDS OF VARIED ETIOLOGY.
Wound Microbiology and Associated Approaches to Wound Management, P. G. Bowler, et al. Clin Microbiol Rev. 2001 April; 14(2): 244-269.

| Aerobic and facultative microorganisms | Type of wound | Anaerobic bacteria | Type of wound |
|---|---|---|---|
| Coagulase-negative *staphylococci* | A, C | *Peptostreptococcus asaccharolyticus* | A, C |
| *Micrococcus* sp. | C | *Peptostreptococcus anaerobius* | A, C |
| *Staphylococcus aureus* | A, C | *Peptostreptococcus magnus* | A, C |
| Beta-hemolytic *streptococcus* (group C) | A | *Peptostreptococcus micros* | A, C |
| Beta-hemolytic *streptococcus* (group G) | C | *Peptostreptococcus prevotii* | A, C |
| *Streptococcus* spp. (fecal) | A, C | *Peptostreptococcus indolicus* | C |
| *Streptococcus* spp. (viridans) | A, C | *Peptostreptococcus* sp. | A, C |
| *Corynebacterium xerosis* | C | *Streptococcus intermedius* | C |
| *Corynebacterium* sp. | A, C | *Clostridium perfringens* | A, C |
| *Bacillus* sp. | A | *Clostridium clostridioforme* | A, C |
| *Escherichia coli* | A, C | *Clostridium cadaveris* | A, C |
| *Escherichia hermanii* | A | *Clostridium baratii* | C |
| *Serratia liquefaciens* | C | *Clostridium septicum* | A |
| *Klebsiella pneumoniae* | A, C | *Clostridium histolyticum* | A, C |
| *Klebsiella oxytoca* | A, C | *Clostridium tertium* | A |

TABLE 1-continued

AEROBIC AND ANAEROBIC ISOLATES FROM ACUTE AND CHRONIC
WOUNDS OF VARIED ETIOLOGY.
Wound Microbiology and Associated Approaches to Wound Management, P. G. Bowler, et
al. Clin Microbiol Rev. 2001 April; 14(2): 244-269.

| Aerobic and facultative microorganisms | Type of wound | Anaerobic bacteria | Type of wound |
|---|---|---|---|
| *Enterobacter cloacae* | A, C | *Clostridium ramosum* | C |
| *Enterobacter aerogenes* | C | *Clostridium sporogenes* | A, C |
| *Citrobacter freundii* | C | *Clostridium difficile* | C |
| *Proteus mirabilis* | A, C | *Clostridium bifermentans* | A |
| *Proteus vulgaris* | C | *Clostridium limosum* | A |
| *Providencia stuartii* | A | *Eubacterium limosum* | C |
| *Morganella morganii* | C | *Propionibacterium acnes* | A, C |
| *Acinetobacter calcoaceticus* | A, C | *Bacteroides fragilis* | A, C |
| *Pseudomonas aeruginosa* | A, C | *Bacteroides ureolyticus* | A, C |
| *Stenotrophomonas maltophilia* | A | *Bacteroides ovatus* | A |
| *Sphingobacterium multivorum* | C | *Bacteroides uniformis* | A, C |
| *Candida parapsilosis* | A | *Bacteroides stercoris* | C |
| *Candida krusei* | A | *Bacteroides capillosus* | C |
| | | *Bacteroides thetaiotaomicron* | C |
| | | *Bacteroides caccae* | C |
| | | *Prevotella oralis* | A, C |
| | | *Prevotella oris* | A, C |
| | | *Prevotella disiens* | A |
| | | *Prevotella bivia* | C |
| | | *Prevotella buccae* | C |
| | | *Prevotella* sp. | A |
| | | *Prevotella corporis* | A, C |
| | | *Prevotella intermedia* | A |
| | | *Prevotella melaninogenica* | C |
| | | *Porphyromonas asaccharolytica* | A, C |
| | | Gram-negative pigmented *bacillus* | A, C |
| | | *Fusobacterium necrophorum* | C |
| | | *Veillonella* spp. | A |

Acute wounds (A) included primarily cutaneous abscesses and postsurgical wounds; chronic wounds (C) included primarily leg ulcers, foot ulcers, and pressure sores. A total 367 isolates were cultured from 106 wounds (61 acute wounds and 45 chronic wounds)

Alternatively, the target microorganism may be selected from aerobic or anaerobic isolates identified in the subject's wound. The following aerobic and facultative or anaerobic microorganism are known isolates from infected wounds, *Streptococcus pyogenes, Staphylococcus aureus*/Methicillin-resistant *Staphylococcus aureus* (MRSA), *Pseudomonas aeruginosa*, and *Eterococci/Vancomycin*-resistant Enterococci (VRE), *Clostridium difficile, Escherichia coli, Klebsiella pneumoniae, Acinetobacter baumannii, Stenotrophomonas maltophilia, Burkholderia cepacia*, and *Ralstonia picketti*.

The nanoparticles may be metal nanoparticle, a nanoparticle with a core-shell structure, or an electroceramic nanocomposite. Such as metal nanoparticles, for example gold nanoparticles, also referred to as AuNP, silver nanoparticles, titanium nanoparticles, or may be carbon-based nanoparticles, such as for example graphene oxide based or carbon nanoparticles like carbon nanotubes or carbon dots with metal shell. The nanoparticles must fulfil the requirement of having an electron density that can couple with a photon wave of electromagnetic radiation. Different surface charges may be applied, such as for example the structure may be anionic, neutral or cationic. The nanoparticles may be functionalized with ligands. In some embodiments, the particles may have a functionalized surface Such surface functionalization may be any suitable surface functionalization such as for example for improving colloidal stability, for obtaining a certain surface charge, for coupling of antimicrobial agents, for targeting. In some particular examples, such polyethylene amine (PEI), polyethyleneglycol, polysaccharides, lectins, antibodies, peptides, aptamers. For example. Spherical n-hydroxysuccinimide (NHS)-activated GNPs may be used to conjugate with anti-*S. aureus* antibodies or anti-*P. aeruginosa* antibodies.

Obtaining a composition into a microbiological film may include allowing the composition to diffuse into the microbiological film following topical administration (dispensing, flowing over) or actively depositing the composition into the microbiological film, such as by injecting or by ballistically propelling the composition into the microbiological film.

The method also comprises, according to embodiments of the present invention, irradiating the microbiological film by said electromagnetic radiation such as to form a vapour bubble using the nanoparticle in the bacterial biofilm. In some embodiments, the vapour bubbles may be water vapour bubbles caused by heating of water around the nanoparticles. In the advantageous embodiments wherein pulsed irradiation is used, the pulse may have a duration in the range 12 ns down to 0.1 ns or down to 0.1 ps. The fluence may be adapted depending on the pulse duration. In one example, the fluence may be at least 10 or tens mJ per pulse. The wavelength of the radiation used may range from UV to the IR region. In some applications, the wavelength range of the radiation used may be between 532 nm and 1064 nm. One or more pulses could be used for inducing the effect. In some embodiment, the pulse width is set at 10-12 nanoseconds at a pulse rate of 1 pulse/second resulting in approximately at 1 j/cm2 energy density.

The irradiation thereby is performed such that the heating of the nanoparticles results in the generation of a mechanical force for locally altering or disrupting said microbiological film when said vapour nanobubble expands and/or collapses. It is to be noticed that the vapour bubbles do not need to explode or implode but that also the fact of expanding or increasing their volume may cause an altering or disrupting effect. It provides a good alternative for direct heating of biofilms, where there is a risk of causing aspecific thermal damage to the surrounding healthy tissue.

The antimicrobial agent used for the present method may be an antiseptics, an antibiotics. In some embodiment, one or more antibiotics may be used in combination with targeted GNP therapy. The antibiotics is selected based on their known effectiveness against the microorganisms known to associate with wound infection or biofilm formation or against the microorganism isolates identified from the subject's wound. Examples of widely used antibiotics include but not limited to from the group consisting of Cephalexin, gentamicin, Augmentin and amikacin. Table 2 shows Topical Antibiotic Products Available for Treating Chronic Wounds (Clinical Infectious Diseases, Volume 49, Issue 10, 15 Nov. 2009, Pages 1541-1549), which may be selected for use in the present method.

In other embodiments of the present invention, one or more antiseptics may also be used, which can be selected from the group consisting of alcohols, quaternary ammonium compounds, chlorhexidine and other diguanides, antibacterial dyes, chlorine and hypochlorites, inorganic iodine compounds, metals, peroxides and permanganates, halogenated phenol derivatives and quinolone derivatives. Table 3 shows topical Antiseptic Products Available for Treating Chronic Wounds (Clinical Infectious Diseases, Volume 49, Issue 10, 15 Nov. 2009, Pages 1541-1549), which may be selected for use in the present method.

The antimicrobial agents may be administered prior, during or after targeted GNP therapy, and may administered where the method is by any route, e.g., intarespiratory, nasal, topical, oral, intravenous, intraperitoneal, intramuscular, transmucosal, buccal, rectal, vaginal, or sublingual.

In yet another aspect, the present invention relates to a method for eradicating a microbiological film, partially by altering and/or disrupting a microbiological film via photothermal and photoacoustic forces.

The microbiological film may for example be a bacterial biofilm, but embodiments are not limited thereto. The present method advantageously finds its application in for example wound healing, although embodiments are not limited thereto. Whereas in embodiments of the present invention reference is made to disruption or altering of microbiological films, such as bacterial films, in healthcare applications, the present invention is equally applicable to biofouling applications, such as for example disruption or altering of films in industrial applications (e.g. brewing, water cleaning etc.)

According to embodiments of the present invention, the method comprises A method for eradicating a microbiological film, the method comprises a) introducing a composition into a microbiological film, the composition comprising nanoparticles having an electron density that can couple with a photon wave of electromagnetic radiation wherein said nanoparticles are capable of binding to one or more target microorganisms; b) irradiating said microbiological film by said electromagnetic radiation such as to generating a mechanical force for locally disrupting said microbiological film; and c) administering to said microbiological film one or more antimicrobial agent.

According to embodiments of the present invention, the target microorganism may be an aerobic and facultative or anaerobic microorganism known to associates with wound infection. Table 1 shows aerobic and anaerobic isolates identified from acute and chronic wounds of varied etiology.

Alternatively, the target microorganism may be selected from aerobic or anaerobic isolates identified in the subject's wound. The following aerobic and facultative or anaerobic microorganism are known isolates from infected wounds, *Streptococcus pyogenes, Staphylococcus aureus/Methicillin*-resistant *Staphylococcus aureus* (MRSA), *Pseudomonas aeruginosa*, and *Enterococci/Vancomycin*-resistant *Enterococci* (VRE), *Clostridium difficile, Escherichia coli, Klebsiella pneumoniae, Acinetobacter baumannii, Stenotrophomonas maltophilia, Burkholderia cepacia*, and *Ralstonia picketti*.

The nanoparticles may be metal nanoparticle, a nanoparticle with a core-shell structure, or an electroceramic nanocomposite. Such as metal nanoparticles, for example gold nanoparticles, also referred to as AuNP, silver nanoparticles, titanium nanoparticles, or may be carbon-based nanoparticles, such as for example graphene oxide based or carbon nanoparticles like carbon nanotubes or carbon dots with metal shell. The nanoparticles must fulfil the requirement of having an electron density that can couple with a photon wave of electromagnetic radiation. Different surface charges may be applied, such as for example the structure may be anionic, neutral or cationic. The nanoparticles may be functionalized with ligands. In some embodiments, the particles may have a functionalized surface. Such surface functionalization may be any suitable surface functionalization such as for example for improving colloidal stability, for obtaining a certain surface charge, for coupling of animicrobial agents, for targeting. In some particular examples, such polyethylene amine (PEI), polyethyleneglycol, polysaccharides, lectins, antibodies, peptides, aptamers. For example, Spherical n-hydroxysuccinimide (NHS)-activated GNPs may be used to conjugate with anti-*S. aureus* antibodies or anti-*P. Aerughnosa* antibodies.

Obtaining a composition into a microbiological film may include allowing the composition to diffuse into the microbiological film following topical administration (dispensing, flowing over) or actively depositing the composition into the microbiological film, such as by injecting or by ballistically propelling the composition into the microbiological film.

The method also comprises, according to embodiments of the present invention, irradiating the microbiological film by said electromagnetic radiation such as to form a vapour bubble using the nanoparticle in the bacterial biofilm. In some embodiments, the vapour bubbles may be water vapour bubbles caused by heating of water around the nanoparticles. In the advantageous embodiments wherein pulsed irradiation is used, the pulse may have a duration in the range 12 ns down to 0.1 ns or down to 0.1 ps. The fluence may be adapted depending on the pulse duration. In one example, the fluence may be at least 10 or tens mJ per pulse. The wavelength of the radiation used may range from UV to the IR region. In some applications, the wavelength range of the radiation used may be between 532 nm and 1064 nm. One or more pulses could be used for inducing the effect. In some embodiment, the pulse width is set at 10-12 nanoseconds at a pulse rate of 1 pulse/second resulting in approximately at 1 j/cm2 energy density.

The irradiation thereby is performed such that the heating of the nanoparticles results in the generation of a mechanical force for locally altering or disrupting said microbiological film when said vapour nanobubble expands and/or collapses. It is to be noticed that the vapour bubbles do not need to explode or implode but that also the fact of expanding or increasing their volume may cause an altering or disrupting effect. It provides a good alternative for direct heating of biofilms, where there is a risk of causing aspecific thermal damage to the surrounding healthy tissue.

The antimicrobial agent used for the present method may be an antiseptics, an antibiotics. In some embodiment, one or more antibiotics may be used in combination with targeted GNP therapy. The antibiotics is selected based on their known effectiveness against the microorganisms known to associate with wound infection or biofilm formation or against the microorganism isolates identified from the subject's wound. Examples of widely used antibiotics include but not limited to from the group consisting of Cephalexin, gentamicin, Augmentin and amikacin. Table 2 shows Topical Antibiotic Products Available for Treating Chronic Wounds (Clinical Infectious Diseases, Volume 49, Issue 10, 15 Nov. 2009, Pages 1541-1549), which may be selected for use in the present method.

In other embodiments of the present invention, one or more antiseptics may also be used, which can be selected from the group consisting of alcohols, quaternary ammonium compounds, chlorhexidine and other diguanides, antibacterial dyes, chlorine and hypochlorites, inorganic iodine compounds, metals, peroxides and permanganates, halogenated phenol derivatives and quinolone derivatives. Table 3 shows topical Antiseptic Products Available for Treating Chronic Wounds (Clinical Infectious Diseases, Volume 49, Issue 10, 15 Nov. 2009, Pages 1541-1549), which may be selected for use in the present method.

The antimicrobial agents may be administered prior, during or after targeted GNP therapy, and may administered where the method is by any route, e.g., intrarespiratory, nasal, topical, oral, intravenous, intraperitoneal, intramuscular, transmucosal, buccal, rectal, vaginal, or sublingual.

Example 1: Effectiveness of Treatment Against Biofilm Using Targeted GNP Laser Therapy and/or Antibiotics In this study, we evaluated the ability of GNP-targeted ns-pulsed laser therapy to eradicate Multidrug Resistance (MDR) *S. aureus* and *Pseudomonas aeruginosa* biofilms, and assessed the benefit of combining this therapy with antibiotics in treating MDR bacterial infections.

*Methicillin*-resistant *Staphylococcus aureus* (MRSA) was selected for this study because it is considered one of the leading causes of chronic biofilm-related infections in U.S. military personnel and civilian populations worldwide [5, 25]. The applicability of this technology for eradication of gram-negative pathogens was investigated using biofilms of MDR *Pseudomonas aeruginosa*, which is responsible for 80% of serious infections in the critically ill and 25%-60% of deaths in infected patients [26].

Methods
A) Materials.

Two MDR clinical wound isolates, namely, methicillin-resistant *S. aureus* (MRSA) SA5120 and *P. aeruginosa* PA 60-65, were received as gifts from a repository at the U.S. Army Institute of Surgical Research (JBSA-Fort Sam Houston, Tex.). Anti-*Staphylococcus aureus* peptidoglycan antibodies (Cat. No. BM3066B) were obtained from Origene (Rockville, Md.), anti-*Pseudomonas aeruginosa* antibodies (Cat. No. ab69232) were purchased from Abcam (Cambridge, Mass.), and 40-nm spherical n-hydroxysuccinimide (NHS)-activated GNPs (Cat. No. C1-40) and 40-nm negative control GNPs (Cat No. C11-40-NC) were purchased from Nanopartz, Inc. (Loveland, Colo.). Papain (Cat. No. P3375), β-mannosidase (Cat. No. M9400), gentamicin (Cat. No. G1264), amikacin (Cat. No. 1019494), sodium phosphate monobasic dihydrate (Cat. No. 71505), and sodium phosphate dibasic heptahydrate (Cat. No. 431478) were purchased from Sigma Aldrich (St. Louis, Mo.). *Vancomycin* (Cat. No. BP 2958-1) was purchased from Fisher Scientific (Hanover Park, Ill.). Concanavalin-A-Alexa Fluor® 488 (Con-A), 4', 6-diamidino-2-phenylindole (DAPI), and Pro-Long™ Gold Antifade Mountant were purchased from Life Technologies (Carlsbad, Calif.). Tryptic soy broth (TSB) was purchased from BD Diagnostics (Sparks, Md.). Tryptic soy agar (TSA) plates were purchased from Hardy Diagnostics (San Maria, Calif.). Phosphate buffered saline (PBS) and Brain Heart Infusion broth (BHI) were purchased from Acumedia (Lansing, Mich.). Glass discs (5-mm diameter) were purchased from Ace Glass, Inc. (Vineland, N.J.), 96-well half-area glass-bottom plates (4.5-mm well diameter, Cat. No. 4580) were purchased from Corning Inc. (Corning, N.Y.), and 96-well full-area glass-bottom plates (6.3-mm well diameter, Cat. No. 164588) were purchased from Thermo Scientific (Waltham, Mass.). Hexamethyldisilazane (Cat. No. 16700) and 25% glutaraldehyde (Cat. No. 16220) were purchased from Electron Microscopy Sciences (Hatfield, Pa.).

B) Preparation of MRSA and *P. aeruginosa* Biofims

Two MDR clinical wound isolates, namely, methicillin-resistant *S. aureus* (MRSA) SA5120 and *P. aeruginosa* PA 60-65, were received as gifts from a repository at the U.S. Army Institute of Surgical Research (JBSA-Fort Sam Houston, Tex.). Biofilms were established on 5-mm glass discs or in 96-well half-area glass-bottom plates that had been pre-treated for 24 h with 1 mg/mL of fibrinogen. Overnight cultures of SA5120 in tryptic soy broth (TSB) were diluted to an optical density at 600 nm ($OD_{600}$) of 0.1 using TSB supplemented with 10% human plasma, added to empty wells of a 96-well glass-bottom culture plate or to wells containing 5-mm glass discs, and allowed to grow into biofilms for 24 h at 37° C. under static conditions. For PA 60-65, overnight cultures in brain heart infusion broth (BHI) were diluted 20-fold using 20% BHI in phosphate-buffered saline (PBS) supplemented with 0.2% glucose and 0.4% NaCl and grown to an $OD_{600}$ of 0.5 at 37° C. with shaking at 250 rpm. The bacterial suspension was diluted to an $OD_{600}$ of 0.01 in PBS, and 20 µL of inoculant was spotted onto 5-mm glass discs placed in 6-well tissue culture plates. Samples were incubated at room temperature for 2 h to allow cell attachment, rinsed in PBS, and then cultured in 20% BHI/0.2% glucose/0.4% NaCl in PBS for 72 h at 37° C. with shaking at 140 rpm. Biofilms were rinsed in PBS and transferred into 96-well glass-bottom plates for subsequent treatment.

C) Preparation of tGNPs

Spherical n-hydroxysuccinimide (NHS)-activated GNPs (40 nm) were reconstituted at 7 mg/mL in ethanol, sonicated, and stored at −20° C. until use. GNP-antibody conjugates were prepared against SA5120 and PA 60-65 by mixing the reconstituted NHS-activated GNPs with anti-*S. aureus* antibodies or anti-*P. aeruginosa* antibodies, respectively, in PBS. The n-hydroxysuccinimide (NHS) groups of activated GNPs react with primary amine groups (—NH2) on the antibody to form a covalent bond. Reaction mixtures were incubated at room temperature for 2 hours with shaking and then centrifuged. The GNP-antibody conjugates were re-suspended in PBS and used as the tGNP stock solution. Spherical 40-nm GNPs containing non-reactive methyl groups were utilized in experiments as non-targeted GNPs.

D) Determination of Optimal Laser Dosage and tGNP Concentration

MRSA biofilms in 96-well glass-bottom plates or on 5-mm glass discs were pre-treated with increasing concentrations of tGNPs from 0-100 µg/mL in PBS for 2 h. This 2-h treatment duration was selected based upon results from comparison of the extent of biofilm dispersion caused by different tGNP incubation periods used in combination with laser irradiation (FIG. 9). Following the tGNP pre-treatment, unattached tGNPs were washed away using PBS, and 40 μL of PBS was added to the wells. Biofilms were then irradiated with increasing numbers of laser pulses from 0-100 pulses at 532 nm and a fluence of ~1.0 J/cm$^2$ using an Nd:YAG laser system (8-ns pulse, 1 Hz; Quantel, Bozeman, Mont.) and an automated XY-gantry sample positioning system operated through LabVIEW software (National Instruments, Austin, Tex.). After exposure, samples were analyzed using confocal microscopy or colony forming unit (CFU) assays.

E) Comparison of tGNPs and Non-Targeted GNPs for Laser Therapy

Biofilms grown on glass discs were pre-treated with tGNPs or non-targeted GNPs at 70 μg/mL in PBS for 2 h (SA5120) or 1 h (PA 60-65). The 1-h pre-treatment period for PA 60-65 was selected based upon results from comparison of biofilm dispersion caused by various tGNP incubation times used in combination with laser irradiation (FIG. 10). Following the tGNP pre-treatment, samples were rinsed using PBS, and 40 μL of PBS was added to each well. Biofilms were then exposed to 50 laser pulses at 532 nm or sham exposed as described in Supplementary Materials. Biofilms treated with 50 laser pulses alone or PBS alone (controls) were also included. Initial pilot experimentation showed that bare GNPs or tGNPs alone (no laser irradiation) had no effect on the bacterial viability of SA5120 and PA 60-65 biofilms (FIG. 11), and thus these treatment conditions were not included in subsequent experiments. After treatment, samples were analyzed using confocal microscopy, CFU assays, or scanning electron microscopy (SEM).

F) Combination of GNP-Targeted Laser Therapy and Antibiotic Treatment

Biofilms on glass discs were pre-treated with tGNPs at 70 μg/mL in PBS for 2 h (SA5120) or 1 h (PA 60-65). Samples were rinsed with PBS, 40 μL of PBS was added to each well, and biofilms were then exposed to 50 laser pulses at 532 nm or sham exposed. Biofilms treated with 50 laser pulses alone or PBS alone were also included. Upon completion of laser or sham exposures, SA5120 biofilms were treated with gentamicin, and PA 60-65 biofilms were treated with amikacin. Specific antibiotics and concentrations were selected based on susceptibilities of the respective planktonic cultures to the antibiotics. Antibiotic solutions were prepared at 2-fold the target concentration using TSB for SA5120 or 20% BHI/0.2% glucose/0.4% NaCl in PBS for PA 60-65, and 40 μL of the appropriate solution was added into sample wells containing biofilms in 40 μL of PBS, resulting in a 1× antibiotic concentration. Samples were incubated for 24 h at 37° C. and then analyzed using CFU assays or SEM.

G) Confocal microscopy analysis

Biofilms were rinsed with PBS and stained with 50 mM of Concanavalin-A-ALEXA FLUOR® 488 (Con-A) for 30 min and 0.5 μg/mL of 4', 6-diamidino-2-phenylindole (DAPI) for 5 min at room temperature. PROLONG™ Gold Antifade reagent was added to the samples and biofilms were imaged using a Nikon Eclipse C1 confocal laser scanning microscope (Nikon, Melville, N.Y.). Images of biofilms were acquired at five non-overlapping fields of view (FOVs) per sample using a 20× objective lens. In biofilms treated with tGNPs followed by laser irradiation, a central damage zone surrounded by an area of residual biofilm was observed; the five FOVs were randomly selected from the central damage zone in these samples. Otherwise, images were acquired from randomly selected FOVs in the central portion of the biofilms. ImageJ software (NIH, Bethesda, Md.) was used to quantitate the fraction of the surface area covered by biofilm in the images. Data were expressed as a percentage of the controls and reported as "substratum coverage (% control)" in the results. Additional details of this method are provided in Supplementary Materials.

H) SFM Analysis

Biofilms on 5-mm glass discs were fixed and processed for SEM analysis as previously described [25]. In brief, biofilms were fixed with 2.5% glutaraldehyde in 0.1 M phosphate buffer (pH 7.3) for 1 h at 4° C. and washed thrice with 0.1 M phosphate buffer for 10 min each. Samples were dehydrated using graded ethanol/water mixtures of 50%, 70%, 80%, 90%, 95% and 100% for 10 min each; 100% ethanol three times for 10 min each; and 50% (v/v) hexamethyldisilazane in ethanol for 1 h. Biofilms were air-dried overnight, sputter coated with gold, and imaged using a ZEISS Sigma VP40 field emission scanning electron microscope (Carl Zeiss, Inc., Germany).

I) CFU Assays

Biofilm-containing discs were rinsed in PBS and placed into petri dishes. For SA5120, 20 μL of papain at 100 μg/mL in PBS was spotted onto the biofilm surface and samples were incubated at room temperature for 30 min. For PA 60-65, 20 μL of β-mannosidase at 0.0225 U/mL in PBS was spotted onto the biofilm surface and samples were incubated at room temperature for 2 h. Loosened biofilms were aspirated and collected in 1.5-mL microfuge tubes. Discs were rinsed thrice using 20 μL of PBS and the washes were pooled into the microfuge tubes. The pooled fractions were sonicated (Qsonica, LLC, Newtown, Conn.) at 6-8 W of output power for 2 min, centrifuged to pellet the cells, and re-suspended in 1 mL of PBS. Samples were serially diluted in PBS, plated in duplicate or triplicate on tryptic soy agar (TSA) plates, and incubated overnight at 37° C. The resulting colonies were enumerated and expressed as CFUs/mL.

For planktonic bacteria, broth cultures of SA5120 in TSB and PA 60-65 in BHI were grown for 16-18 h at 37° C. on a shaker at 250 rpm. The cultures were diluted to an $OD_{600}$ of 0.1 using TSB for SA5120 or BHI for PA 60-65 and incubated at 37° C. for ~1.5 h to reach an $OD_{600}$ of 0.3. Samples were treated with antibiotics in triplicate in 5-mL tubes at 37° C. on a shaker at 250 rpm for 24 h, after which 1 mL of culture from each tube was transferred into a fresh tube and centrifuged to pellet the cells. The cell pellets were washed twice in PBS, re-suspended in 1 mL of PBS, serially diluted in PBS, and plated in triplicate on TSA plates. The plates were incubated overnight at 37° C., and the resulting colonies were enumerated and used to calculate CFUs/mL.

J) Statistical Analysis

Data are presented as the mean±standard deviation. For CFU assay results, 0 values were replaced with the lowest observed value in each set of experiments, which was considered the lower limit of detection, and data were log 2 transformed. GraphPad Prism 6 (version 6.04, La Jolla, Calif.) was used to compare groups via the Student's t test, and $p<0.05$ was considered significant.

Results

Nanoparticle-assisted laser therapy is envisioned as a strategy to disrupt the biofilm architecture and, resultantly, remove a significant barrier that limits diffusion of antibiotics to bacteria in deeper layers of the biofilm. Increasing access of oxygen and other nutrients to biofilm-resident cells via this approach may also increase sensitivity of bacteria to antibiotics [7]. FIG. 1 is a schematic illustration of this approach in which GNP-antibody conjugates selectively bind to the biofilm surface, and when irradiated with 532 nm visible light, amplify laser energy absorption leading to extremely rapid heating (photothermal effect) and generation of acoustic waves (opto-acoustic effect) around the particles [22]. This phenomenon leads to thermal and mechanical damage to the extracellular matrix and bacteria and, ultimately, destruction of the biofilm.

A) Optimal Laser Dosage and tGNP Concentration

Confocal microscopy analysis of MRSA biofilms in 96-well plates revealed that pre-treatment with 70 μg/mL of tGNPs followed by irradiation with 50 laser pulses resulted in uniform dispersion of the biofilms (FIG. 2A). Treatment with fewer numbers of pulses or lower tGNP concentrations led to incomplete biofilm dispersion, and increasing the number of pulses or the GNP concentration did not significantly increase the extent of biofilm dispersion. Viability assays of MRSA biofilms on glass discs confirmed that treatment of biofilms with 70 μg/mL of tGNPs plus 50 pulses of laser energy led to a significant reduction of CFUs relative to untreated controls, and increasing the doses to >50 pulses or >70 μg/mL of tGNPs did not significantly increase bacterial cell killing (FIG. 2B). Thus, a tGNP concentration of 70 μg/mL and 50 laser pulses were selected for use in subsequent experiments. In addition, pilot experiments in which bacterial viability was determined in the dosing solutions as well as in the biofilms after treatment confirmed that the decrease in CFUs in biofilms treated with tGNPs plus laser irradiation was mainly due to bacterial killing rather than only dispersal of cells into the culture medium (data not shown).

B) Comparison of tGNPs and Non-Targeted GNPs for Laser Therapy

To confirm targeted dispersion of biofilms was achievable using antibody-conjugated GNPs, biofilms on glass discs were used to evaluate the efficacy of laser therapy on samples pre-treated with tGNPs versus groups pre-treated with non-targeted GNPs. Confocal micrographs of MRSA biofilms showed that control samples were composed of a continuous layer of matrix polysaccharides and bacterial cells (FIG. 3A). Treatment of MRSA biofilms with tGNPs plus pulsed laser irradiation led to the highest dispersion of biofilms as indicated by the sparse green and blue staining in the images (FIG. 3A). ImageJ analysis of the confocal micrographs showed that this treatment resulted in removal of 96±3% of the biofilms (matrix and cells) compared to controls (FIG. 3B). In contrast, treatment of MRSA biofilms with non-targeted GNPs followed by laser or with laser alone removed <1% of the biofilms relative to the controls (FIG. 3B), indicating successful antibody-targeting of the GNPs to the biofilms.

For PA 60-65, confocal micrographs showed a robust, continuous layer of biofilm in controls and samples treated with laser irradiation alone (FIG. 3C). Interestingly, treatment with tGNPs or non-targeted GNPs plus 50 pulses of laser irradiation both led to extensive dispersion, suggesting a significant level of non-specific binding of GNPs to the $P.$ $aeruginosa$ biofilms that may be due to the mucoid nature of this bacterial species [26]. ImageJ analysis of the micrographs confirmed that treatment with tGNPs or non-targeted GNPs plus laser irradiation resulted in the removal of 99±0.2% of PA 60-65 biofilms (FIG. 3D). Based on these observations, ICP-MS was used to determine the level of bare GNP and tGNP binding to $S.$ $aureus$ and $P.$ $aeruginosa$ biofilms. Results indicate a statistically significant difference in the amount of bare GNP and tGNP binding to $S.$ $aureus$ biofilms, but no difference in binding of bare GNPs and tGNPs to $P.$ $aeruginosa$ biofilms (FIG. 13). Thus, the ICP-MS data are in agreement with the confocal microscopy and viability (CFU) data, which all indicate more non-specific binding of non-targeted (bare) GNPs to $P.$ $aeruginosa$ biofilms.

C) Effect of GNP-Targeted Laser Therapy on Biofilm Viability and Morphology

CFU assays showed that treatment of MRSA biofilms with tGNPs plus laser irradiation led to ~1-log reduction in bacterial viability (90% cell killing), while treatment with laser irradiation alone or non-targeted GNPs plus laser did not cause a significant decrease in biofilm viability relative to controls (FIG. 4A). Treatment of $P.$ $aeruginosa$ biofilms with tGNPs plus laser resulted in a 1.6-log reduction in viability, and treatment with non-targeted GNPs plus laser led to ~1-log reduction in viability, both of which were statistically significant relative to controls (FIG. 4B). Thus, data from the CFU assays were in agreement with the results of the confocal microscopy analysis shown in FIG. 3.

SEM micrographs of MRSA biofilms at 50× magnification revealed that control samples and samples exposed to laser irradiation alone exhibited intact biofilms with no apparent damage (FIG. 4C, top row of images). In contrast, treatment with tGNPs plus laser irradiation led to significant dispersion of the biofilm matrix and detachment of bacterial cells from the glass surface as shown by a cleared 'damage zone' surrounded by residual biofilm on the outermost edges of the glass discs. This pattern is likely due to the Gaussian distribution of energy in the laser beam that is expected to cause maximal biofilm disruption in the area of highest laser energy deposition. When visualized at 30,000× magnification (FIG. 4C, bottom row of images), no overt cell membrane damage was observed in the bacteria remaining on the discs after exposure to GNP-targeted laser therapy, suggesting the residual cells were viable (FIG. 4C). However, these biofilms did show areas in which cells and extracellular matrix appeared to have been dispersed (red arrows in FIG. 4C), in contrast to controls and samples treated with laser irradiation alone that exhibited more extensive amounts of extracellular matrix material.

D) GNP-Targeted Laser Therapy Synergized with Gentamicin Against MRSA Biofilms

The benefit of combining GNP-targeted laser therapy with antibiotic treatment was determined by assessing the effects of combination therapy on bacterial viability and dispersion of biofilms. Treatment of MRSA biofilms with GNP-targeted pulsed laser therapy followed by 24-h gentamicin treatment at 100 μg/mL caused a 4-log reduction in viable bacteria (99.99%), whereas treatment with gentamicin alone or GNP-targeted laser therapy alone resulted in only a 1-log reduction in viability compared to untreated controls (FIG. 5A). Thus, combining GNP-targeted laser therapy and gentamicin treatment led to a synergistic enhancement of effect against the MRSA biofilms. Notably, this 4-log reduction in biofilm viability was similar to that observed in planktonic MRSA SA5120 cultures treated with gentamicin (FIG. 5B), suggesting that the GNP-targeted laser therapy effectively dispersed the biofilm matrix allowing the antibiotic to access and kill the bacteria. Treating MRSA biofilms with gentamicin at 100 μg/mL for 48 h instead of 24 h following GNP-targeted therapy did not increase the antibacterial effect of the combination treatment (FIG. 14). It was also noted that GNP-targeted laser therapy enhanced the antibacterial activity of 24-h vancomycin treatment at 100 or 1000 μg/mL against MRSA biofilms, though the effect was less pronounced than with gentamicin (FIG. 15).

SEM imaging confirmed that treatment of MRSA biofilms with the combination of GNP-targeted laser therapy and gentamicin resulted in dispersion of the biofilm matrix and bacteria from the glass surface, particularly in the 'damage zone' that is presumed to be the site of highest laser energy deposition (FIG. 5C). In contrast, biofilms treated with gentamicin alone showed no apparent alterations in the integrity of the biofilms (top row of images in FIG. 5C), as indicated by a lack of a damage zone on the disc (50× magnification) and presence of extracellular matrix (30,000× magnification), and resembled the SEM image of the control biofilm in FIG. 4C.

E) GNP-Targeted Laser Therapy Synergized with Amikacin Against *P. aeruginosa* Biofims To assess the applicability of GNP-targeted laser therapy against gram-negative bacteria, the effect of combination therapy with amikacin against *P. aeruginosa* biofilms was evaluated. Treatment of *P. aeruginosa* biofilms with GNP-targeted laser therapy alone or 8 µg/mL of amikacin alone for 24 h led to ~1-log reduction in cell viability relative to controls (FIG. 6A). When the biofilms were treated with GNP-targeted laser therapy in combination with 8 µg/mL of amikacin, a 5-log reduction in viability was observed, indicating synergism between the two treatments. Increasing the amikacin concentration from 8 to 16 µg/mL did not further reduce cell viability in biofilms treated with the combination therapy. For comparison, planktonic PA 60-65 cultures treated with 16-64 µg/mL of amikacin for 24 h showed ~4-log reduction in viability compared to controls (FIG. 6B). Taken together, the findings revealed that the combination therapy was as efficacious against biofilms as amikacin alone against *P. aeruginosa* planktonic cultures, further suggesting that GNP-targeted laser therapy effectively disrupts the barrier properties of biofilms and allows antibiotics to access the resident bacteria (FIG. 6B).

DISCUSSION

Achieving therapeutic efficacy against recalcitrant wound infections is largely predicated on overcoming the survival mechanisms of biofilms that significantly reduce the effectiveness of many commonly used antimicrobials [8, 9]. Indeed, treatment regimens that remove biofilms using physical or chemical debridement have been shown to improve clinical outcomes in patients with chronically infected wounds and diabetic ulcers [8, 27]. Most of these techniques, however, do not specifically target infectious material in a wound and may result in significant trauma to vital host tissue. In this report, we investigated GNP-mediated ns-pulsed laser therapy as a novel strategy for targeted destruction of MDR biofilms and enhancement of antibiotic efficacy, an approach that may be useful for limiting collateral host tissue damage.

A major finding of this study is that GNP-targeted laser therapy was able to rapidly disperse 96-99% of the extracellular matrix and cells (FIG. 3) and kill up to ~90-98% of the resident bacteria (FIGS. 4, A and B) in MRSA and MDR *P. aeruginosa* biofilms. Confocal microscopy and SEM analysis revealed the most extensive removal of the MRSA and MDR *P. aeruginosa* biofilms within the main damage zone, which is likely the site of highest laser energy deposition. The images also showed removal of mostly extracellular matrix and fewer of the bacteria on the outer edges of samples, which is expected due to the Gaussian nature of the incident laser beam and possible distortions of the laser beam at the edge of the sample well (FIG. 4C). Thus, the data collectively indicate highly effective removal of biofilm infections in areas subjected to the full laser dosage.

Prior studies with planktonic cultures showed that antibody-targeted GNPs irradiated with ns laser pulses generated highly localized photothermal phenomena at the surface of bacteria [22]. It is likely that the anti-biofilm effects observed in the current investigation were the result of similar photothermally-induced damage mechanisms such as heat- and pressure-induced denaturation, degradation, and disruption of the extracellular matrix and biofilm-associated bacteria. The finding that tGNPs (FIG. 2A) or pulsed laser exposure alone (FIGS. 3 and 4) caused no significant changes to biofilm integrity or viability further indicates the anti-biofilm effects observed in samples treated with the combination of tGNPs and ns-pulsed laser irradiation were due to induction of photothermal phenomena rather than the individual effects of the antibodies, GNPs, or laser irradiation against the biofilms. In addition, no increase in temperature was detected in the dosing solutions in our experiments (FIG. 16), which supports the assertion that use of ns-pulsed laser irradiation generates thermal energy on a ns timescale localized around the GNPs and limits heat diffusion into the surrounding medium.

Another significant finding of the current investigation is that the combination of GNP-targeted pulsed laser therapy with 24-h gentamicin or amikacin treatment led to a synergistic 4- to 5-log reduction in MRSA and *P. aeruginosa* biofilm viability, whereas antibiotics or GNP-targeted laser therapy alone caused only a 1-log reduction in viability (FIGS. 5 and 6). Notably, the level of killing induced by the combination therapy against the biofilms was similar to the reductions in viability observed in planktonic MRSA and *P. aeruginosa* cultures treated with the antibiotics alone. These data suggest that GNP-targeted laser therapy was effective in eradicating the occlusive properties of the extracellular matrix that limit the diffusion of antibiotics to the bacteria within the biofilm. Because drug tolerance has also been attributed to reduced growth rates of nutrient-starved bacteria in deeper layers of the biofilm [7], it is possible that GNP-targeted therapy enhanced antibiotic susceptibility of the biofilms by increasing penetration of oxygen and other nutrients to the underlying bacterial cells.

Overall, our findings agree with prior reports that biofilm-associated bacteria exhibit up to 3 orders of magnitude lower sensitivity to antibiotics than planktonic cultures [4] and decreased penetration of gentamicin and amikacin into biofilms may reduce the antibacterial efficacy of these agents [6]. Furthermore, our data are in agreement with previous observations that dispersal of biofilms rapidly restores susceptibility of bacteria to antibiotics, including gentamicin [6, 28]. Reduced penetration of vancomycin has also been proposed as a mechanism of drug tolerance in *S. aureus* biofilms [29], and GNP-targeted laser therapy did enhance the antibacterial effect of this antibiotic against SA5120 MRSA biofilms. However, the efficacy of GNP-targeted laser therapy combined with vancomycin against SA5120 biofilms (2-log decreased viability) did not reach the level of antibacterial activity of vancomycin against planktonic SA5120 cultures (4-log decreased viability; FIG. 10). This indicates mechanisms other than reduced diffusion through the extracellular matrix may be responsible for the decreased susceptibility of SA5120 biofilms to vancomycin [5, 6], or the biofilms may have started to regrow during the 24-h vancomycin treatment following dispersal by GNP-targeted laser therapy. *Vancomycin*-induced formation of biofilms has been observed in some strains of MRSA [30], and thickened biofilms were observed in some samples treated with vancomycin in the current study (FIG. 10).

The majority of previous investigations of GNP-targeted laser therapy for antimicrobial applications involved the use of planktonic cultures and/or CW laser systems [16-20, 22]. A limited number of studies have reported the anti-biofilm activity of photothermal or acoustic wave effects generated by pulsed laser systems in combination with GNPs, Au@Ag nanoparticles, or antibiotics [31, 32]. For example, Ding et al. found that near-infrared femtosecond-pulsed laser irradiation had no effect on *S. aureus* biofilm viability when combined with GNPs, but caused an 85% reduction in viability in combination with Au@Ag nanoparticles (combination of photothermal and silver effects) [31]. Using a ns-pulsed laser to generate non-thermal shockwaves, Yao et al. observed a 1-log reduction in *Staphylococcus epidermidis* biofilm viability when this therapy was combined with 24-h gentamicin treatment [32]. In comparison, our results revealed that GNP-targeted ns-pulsed laser therapy alone was as effective as these other methods in that it caused a 1-log reduction in bacterial biofilm viability, and in combination with antibiotics, our approach achieved a greater anti-biofilm effect of up to a 5-log decrease in viability.

In conclusion, our findings demonstrate that GNP-targeted laser therapy potentiates the activity of antibiotics against in vitro MRSA and *P. aeruginosa* biofilms via photothermal destruction of the matrix and cellular components of the biofilm.

Prophetic Example: Treatment of Topical Wound Infections

The following investigation is aimed to determine whether the inventive method may be used to selectively eradication of biofilms in a topical wound while minimizing collateral host tissue damage in vivo.

Laboratory animals with chronic open wound were prepared and separated into three groups: targeted GNP, targeted GNP+antimicrobial and antimicribal treatment alone. Wound fluid, swap will be cultured and analyzed to identify microbial isolates. Selecting antimicrobial agents and dosing regimen most effective for the identified isolates. Administering selected antimicrobial agents to targeted GNP+antimicrobial and antimicribal alone groups according to same dosing regimen. Applying targeted GNP therapy according to the present invention to targeted GNP and targeted GNP+antimicrobial groups. Compare the results.

The present invention presented multiple advantages over existing technologies. While Zharov et al. [22] demonstrated the effectiveness of their technology in killing planktonic bacteria. The method's effectiveness against established biofilm, and biofilm infected wound are largely unknown. Zharov et al. also did not teach synergistic effectiveness against biofilm and wound infection by combining targeted GNP with the use of an antimicrobial agent, such as an antibiotics. The present invention successfully demonstrate combined therapeutic effectiveness of targeted GNP and antibiotics.

Meeker [20] et al. showed to some extent the synergistic photothermal and antibiotic killing of biofilm-associated *Staphylococcus aureus*. However, his method is limited as Meeker et al. used gold nanocages (AuNC) containing antibiotics. As not all antimicrobial agents against microorganisms may not be successfully encapsulated by these gold nanocages, the method may prevent the use of the most effective antimicrobial agents against a particular wound infection or type of biofilm. The present invention, on the hand allows for more tailored therapies based on a patient's culture results by permitting a more flexible antimicrobial regimes and timing. Furthermore, Meeker et al. used a continuous wave laser irradiation is used to produce bulk sample heating, which may cause significant heating. It remains unclear whether exposing other type of antibiotics to heating (as Meeker et al did) may reduce therapeutic efficacy. The present method was able kill and disperse biofilm without any measurable increase in sample temperature, which allows a wider range of therapy to be used in combination with targeted GNP therapy.

REFERENCES

1. Roca, I., et al., *The global threat of antimicrobial resistance: science for intervention*. New Microbes New Infect, 2015. 6: p. 22-9.
2. Sanchez, C., et al. *Biofilm formation by clinical isolates and the implications in chronic infections*. BMC Infect Dis, 2013. 13, 47 DOI: 10.1186/1471-2334-13-47.
3. Lebeaux, D., et al., *From in vitro to in vivo models of bacterial biofilm-related infections*. Pathogens, 2013. 2(2): p. 288-356.
4. Saginur, R., et al., *Multiple combination bactericidal testing of Staphylococcal biofilms from implant-associated infections*. Antimicrob Agents Chemother, 2006. 50(1): p. 55-61.
5. Hall-Stoodley, L., J. W. Costerton, and P. Stoodley, *Bacterial biofilms: from the natural environment to infectious diseases*. Nat Rev Microbiol, 2004. 2(2): p. 95-108.
6. Stewart, P.-S., *Mechanisms of antibiotic resistance in bacterial biofilms*. Int J Med Microbiol, 2002. 292(2): p. 107-113.
7. Hall, C. W. and T. F. Mah, *Molecular mechanisms of biofilm-based antibiotic resistance and tolerance in pathogenic bacteria*. FEMS Microbiol Rev, 2017. 41(3): p. 276-301.
8. Metcalf, D. G. and P. G. Bowler, *Biofilm delays wound healing. a review of the evidence*. Burns Trauma, 2013. 1(1): p. 5-12.
9. Rhoads, D. D., R. Wolcott, and S. L. Percival, *Biofilms in wounds: management strategies*. J Wound Care, 2008. 17(11): p. 502-508.
10. Mah, T.-F. C. and G. A. O'Toole, *Mechanisms of biofilm resistance to antimicrobial agents*. Trends Microbiol, 2001. 9(1): p. 34-39.
11. Mocan, L., et al., *Surface plasmon resonance-induced photoactivation of gold nanoparticles as bactericidal agents against methicillin-resistant Staphylococcus aureus*. Int J Nanomedicine, 2014. 9: p. 1453-1461.
12. Jain, P. K., et al., *Review of some interesting surface plasmon resonance-enhanced properties of noble metal nanoparticles and their applications to biosystems*. Plasmonics, 2007.2(3): p. 107-118.
13. Galanzha, E. I., et al., *In vivo magnetic enrichment, photoacoustic diagnosis, and photothermal purging of infected blood using multifunctional gold and magnetic nanoparticles*. PLoS ONE, 2012.7(9): p. e45557.
14. Kirui, D. K., et al., *Targeted near-IR hybrid magnetic nanoparticles for in vivo cancer therapy and imaging*. Nanomedicine: NBM, 2013. 9(5): p. 702-711.
15. Kolovskaya, O. S., et al., *Aptamer-targeted plasmonic photothermal therapy of cancer*. Mol Ther Nucleic Acids, 2017. 9: p. 12-21.
16. Millenbaugh, N.J., et al., *Photothermal killing of Staphylococcus aureus using antibody-targeted gold nanoparticles*. Int J Nanomedicine, 2015. 10: p. 1953-1960.
17. Norman, R. S., et al., *Targeted photothermal lysis of the pathogenic bacteria, Pseudomonas aeruginosa, with gold nanorods*. Nano Lett, 2007. 8(1): p. 302-306.
18. Huang, W. C., P. J. Tsai, and Y. C. Chen, *Functional gold nanoparticles as photothermal agents for selective-killing of pathogenic bacteria*. Nanomedicine (Lond), 2007. 2(6): p. 777-787.

19. Teng, C. P., et al., *Effective targeted photothermal ablation of multidrug resistant bacteria and their biofilms with NIR-absorbing gold nanocrosses.* Adv Healthc Mater, 2016. 5(16): p. 2122-2130.
20. Meeker, D. G., et al., *Synergistic photothermal and antibiotic killing of biofilm-associated Staphylococcus aureus using targeted antibiotic-loaded gold nanoconstructs.* ACS Infect Dis 2016.2: p. 241-250.
21. Yarmolenko, P. S., et al., *Thresholds for thermal damage to normal tissues: an update.* Int J Hyperthermia, 2011. 27(4): p. 320-43.
22. Zharov, V. P., et al., *Photothermal nanotherapeutics and nanodiagnostics for selective killing of bacteria targeted with gold nanoparticles.* Biophys J, 2006. 90(2): p. 619-627.
23. Nathwani, D., et al., *Clinical and economic consequences of hospital-acquired resistant and multidrug-resistant Pseudomonas aeruginosa infections: a systematic review and meta-analysis.* Antimicrob Resist Infect Control, 2004.3(32): p. 1-16.
24. Archer, N. K., et al., *Staphylococcus aureus biofilms: Properties, regulation and roles in human disease.* Virulence, 2011. 2(5): p. 445-459.
25. Araujo, J. C., et al., *Comparison of hexamethyldisilazane and critical point drying treatments for SEM analysis of anaerobic biofilms and granular sludge.* J Electron Microsc 2003. 52(4): p. 429-433.
26. Wagner, S., et al., *Novel strategies for the treatment of Pseudomonas aeruginosa infections.* J Med Chem, 2016. 59(13): p. 5929-5969.
27. Doerler, M., et al., *Impact on wound healing and efficacy of various leg ulcer debridement techniques.* J Dtsch Dermatol Ges, 2012. 10(9): p. 624-632.
28. Hess, D. J., M. J. Henry-Stanley, and C. L. Wells, Gentamicin promotes *Staphylococcus aureus biofilms on silk suture.* J Surg Res, 2011. 170(2): p. 302-8.
29. Singh, R., et al., *Penetration of antibiotics through Staphylococcus aureus and Staphylococcus epidermidis biofilms.* J Antimicrob Chemother, 2010. 65(9): p. 1955-8.
30. Deresinski, S., *Vancomycin heteroresistance and methicillin-resistant Staphylococcus aureus.* J Infect Dis, 2009. 199(5): p. 605-609.
31. Ding, X., et al., *Au-Ag core-shell nanoparticlesfor simultaneous bacterial imaging and synergistic antibacterial activity.* Nanomedicine: NBM, 2017. 13(1): p. 297-305.
32. Yao, W., et al., *Laser-generated shockwaves enhance antibacterial activity against biofilms in vitro.* Lasers Surg Med, 2017. 49(5): p. 539-547.

What is claimed is:

1. A method for treating a wound infection, comprising:
    a) introducing a composition into a wound, said composition comprising nanoparticles having an electron density that can couple with a photon wave of electromagnetic radiation, wherein said nanoparticles are capable of binding to one or more target microorganisms associated with wound infection;
    b) irradiating said wound by said electromagnetic radiation; and
    c) administering one or more therapeutic effective dose of an antimicrobial agent to said subject.
2. The method according to claim 1, wherein said target microorganism is
    a) an aerobic and facultative or anaerobic microorganism known to associates with wound infection; or
    b) an aerobic or anaerobic isolates from said patient's wound.
3. The method according to claim 2, wherein the aerobic and facultative or anaerobic microorganism known to associate with wound infection is selected from the group consisting of *Streptococcus pyogenes, Staphylococcus aureus*/A Methicillin-resistant *Staphylococcus aureus* (MRSA), *Pseudomonas aeruginosa*, Enterococci/Vancomycin-resistant *Enterococci* (VRE), *Clostridium dificile, Escherichia coli, Klebsiella pneumoniae, Acinetobacter baumannii, Stenotrophomonas maltophilia, Burkholderia cepacia*, and *Ralstonia picketti.*
4. The method according to claim 1, wherein said antimicrobial agent is an antiseptic, or an antibiotics.
5. The method according to claim 4, wherein said antibiotics is selected from the group consisting of Cephalexin, gentamicin, Augmentin, and amikacin.
6. The method according to claim 4, wherein said antiseptics is selected from the group consisting of alcohols, quaternary ammonium compounds, chlorhexidine and other diguanides, antibacterial dyes, chlorine and hypochlorites, inorganic iodine compounds, metals, peroxides and permanganates, halogenated phenol derivatives, and quinolone derivatives.
7. The method according to claim 1, wherein said nanoparticle is metal nanoparticle, a nanoparticle with a core-shell structure, or an electroceramic nanocomposite.
8. The method according to claim 7, wherein said metal nanoparticle is a gold nanoparticle or a silica nanoparticle coated with a gold shell.
9. The method according to claim 1, wherein irradiating said wound by said electromagnetic radiation comprises irradiating by a pulsed irradiation source, wherein said pulse of electromagnetic radiation having a pulse length in the range of 10-12 ns at a pulse rate at 1 pulse/second.
10. The method according to claim 1, wherein said nanoparticles have antibodies, and/or aptamers that binds to said target microorganism.
11. A method for eradicating a microbiological film from a surface, the method comprising:
    a) introducing a composition into a microbiological film, the composition comprising nanoparticles having an electron density that can couple with a photon wave of electromagnetic radiation wherein said nanoparticles are capable of binding to one or more target microorganisms associated with the microbiological film;
    b) irradiating said microbiological film by said electromagnetic radiation such as to generate mechanical force for locally disrupting said microbiological film; and
    c) administering to said microbiological film one or more antimicrobial agent.
12. The method according to claim 11, wherein irradiating said microbiological film by said electromagnetic radiation comprises irradiating the microbiological film by a pulsed irradiation source, said pulse of electromagnetic radiation having a pulse length in the range of 10-12 ns at a pulse rate at 1 pulse/second.
13. The method according to claim 11, wherein said microbiological film is any group of microorganisms in which cells stick to each other and cells adhere to a surface.
14. The method according to claim 11, wherein said target microorganism is a bacteria selected from the group consisting of *Streptococcus pyogenes, Staphylococcus aureus/* Methicillin-resistant *Staphylococcus aureus* (MRSA), *Pseudomonas aeruginosa*, Enterococci/Vancomycin-resistant *Enterococci* (VRE), *Clostridium difficile, Escherichia* coli, *Klebsiella pneumoniae, Acinetobacter baumannii, Stenotrophomonas maltophilia, Burkholderia cepacia*, and *Ralstonia picketti*.

15. The method according to claim 11, wherein locally disrupting said microbiological film comprises disrupting the film such that cells become loosened from each other and/or from the surface.

16. The method according claim 11, said nanoparticle is metal nanoparticle, a nanoparticle with a core-shell structure, or an electroceramic nanocomposite.

17. The method of claim 16, wherein said metal nanoparticle is a gold nanoparticle or a silica nanoparticle coated with a gold shell.

18. The method of claim 11, wherein said antimicrobial agent is an antiseptics or an antibiotics.

19. The method of claim 18, wherein said antibiotics is selected from the group consisting of Cephalexin, gentamicin, Augmentin, and amikacin.

20. The method of claim 18, wherein said antiseptic is selected from the group consisting of alcohols, quaternary ammonium compounds, chlorhexidine and other diguanides, antibacterial dyes, chlorine and hypochlorites, inorganic iodine compounds, metals, peroxides and permanganates, halogenated phenol derivatives, and quinolone derivatives.

21. The method according to claim 11, wherein said nanoparticles have antibodies, or aptamer that binds to said target microorganism.

22. The method according to claims 1 or 11, wherein said composition further comprises an adjuvant or a carrier.

23. The method according to claim 1 or 11, wherein said antimicrobial agent is administered topically, subcutaneously, intravenously, intramuscularly or orally.

* * * * *